United States Patent [19]
Yoon

[11] Patent Number: 5,954,731
[45] Date of Patent: Sep. 21, 1999

[54] SURGICAL INSTRUMENT WITH MULTIPLE ROTATABLY MOUNTED SPREADABLE END EFFECTORS

[76] Inventor: InBae Yoon, 2101 Highland Ridge Dr., Phoenix, Md. 21131

[21] Appl. No.: 08/902,311

[22] Filed: Jul. 29, 1997

[51] Int. Cl.$^6$ .................................................. A61B 17/04
[52] U.S. Cl. ........................ 606/144; 606/139; 606/147; 606/148
[58] Field of Search .................................. 606/144, 145, 606/147, 148, 139, 205, 206

[56] References Cited

U.S. PATENT DOCUMENTS

| | | |
|---|---|---|
| 919,138 | 4/1909 | Drake et al. . |
| 1,037,864 | 9/1912 | Carlson et al. . |
| 1,131,163 | 3/1915 | Saunders et al. . |
| 1,155,378 | 10/1915 | Steedman . |
| 1,449,087 | 3/1923 | Bugbee . |
| 1,822,330 | 9/1931 | Ainslie . |
| 1,916,722 | 7/1933 | Ende . |
| 2,213,830 | 9/1940 | Anastasi . |
| 2,580,964 | 1/1952 | Skaller . |
| 2,601,564 | 6/1952 | Smith . |
| 2,646,045 | 7/1953 | Priestley . |
| 2,959,172 | 11/1960 | Held . |
| 3,090,386 | 5/1963 | Curtis . |
| 3,139,089 | 6/1964 | Schwerin . |
| 3,349,772 | 10/1967 | Rygg . |
| 3,470,875 | 10/1969 | Johnson . |
| 3,842,840 | 10/1974 | Schweizer . |
| 3,946,740 | 3/1976 | Bassett . |
| 4,109,658 | 8/1978 | Hughes . |
| 4,164,225 | 8/1979 | Johnson et al. . |
| 4,257,420 | 3/1981 | Terayama . |
| 4,440,171 | 4/1984 | Nomoto et al. . |
| 4,557,265 | 12/1985 | Andersson . |
| 4,621,640 | 11/1986 | Mulhollan et al. . |
| 4,635,638 | 1/1987 | Weintraub et al. . |

(List continued on next page.)

FOREIGN PATENT DOCUMENTS

| | | |
|---|---|---|
| 482881A1 | 4/1992 | European Pat. Off. . |
| 0337579 | 4/1904 | France . |
| 0395073 | 8/1973 | U.S.S.R. . |
| 2260704 | 4/1993 | United Kingdom . |
| WO 97/37583 | 10/1997 | WIPO . |

*Primary Examiner*—Michael Buiz
*Assistant Examiner*—Julian W. Woo
*Attorney, Agent, or Firm*—Blank Rome Comisky & McCauley LLP

[57] ABSTRACT

An instrument for performing a surgical procedure includes a housing, an elongate shaft having a proximal end mounted by the housing and a distal end with a peripheral edge, a first end effector assembly protruding from the distal end of the elongate shaft and having an end effector at a distal end, and a second end effector assembly protruding from the distal end of the elongate shaft and having an end effector at a distal end. Distal portions of the first and second end effector assemblies extend laterally outward at an angle from first and second longitudinal axes of the elongate shaft to positions where at least a portion of the corresponding end effectors are spaced laterally outward of the peripheral edge of the elongate shaft. In addition, the end effector assemblies are rotatable about the first and second longitudinal axes of the elongate shaft to cause the corresponding end effectors to move along first and second arcuate paths. When inserting the surgical instrument through a portal in an endoscopic procedure, the first and second end effector assemblies are preferably moved to undeployed positions where their end effectors are spaced laterally inward of the peripheral edge of the elongate shaft, for example by rotating the end effector assemblies inwardly or drawing the end effectors proximally into the elongate shaft so that they are straightened. In use, the end effectors can be moved from their undeployed positions to deployed positions disposed laterally outward of the peripheral edge due to the angled configuration of the distal portions of the end effector assemblies.

56 Claims, 8 Drawing Sheets

5,954,731
Page 2

U.S. PATENT DOCUMENTS

| | | |
|---|---|---|
| 4,935,027 | 6/1990 | Yoon . |
| 5,037,433 | 8/1991 | Wilk et al. . |
| 5,100,421 | 3/1992 | Christoudias . |
| 5,147,373 | 9/1992 | Ferzli . |
| 5,152,769 | 10/1992 | Baber . |
| 5,171,257 | 12/1992 | Ferzli . |
| 5,181,919 | 1/1993 | Bergman et al. . |
| 5,209,741 | 5/1993 | Spaeth . |
| 5,211,650 | 5/1993 | Noda . |
| 5,222,508 | 6/1993 | Contarini . |
| 5,224,948 | 7/1993 | Abe et al. . |
| 5,234,443 | 8/1993 | Phan et al. . |
| 5,244,948 | 9/1993 | Mulhaupt et al. . |
| 5,261,917 | 11/1993 | Hasson et al. . |
| 5,281,238 | 1/1994 | Chin et al. . |
| 5,300,082 | 4/1994 | Sharpe et al. . |
| 5,304,185 | 4/1994 | Taylor . |
| 5,305,121 | 4/1994 | Moll . |
| 5,308,353 | 5/1994 | Beurrier . |
| 5,320,632 | 6/1994 | Heidmueller . |
| 5,336,230 | 8/1994 | Leichtling et al. . |
| 5,336,231 | 8/1994 | Adair . |
| 5,356,424 | 10/1994 | Buzerak et al. . |
| 5,364,408 | 11/1994 | Gordon ............... 606/144 |
| 5,364,409 | 11/1994 | Kuwabara et al. . |
| 5,374,275 | 12/1994 | Bradley et al. . |
| 5,376,096 | 12/1994 | Foster . |
| 5,389,098 | 2/1995 | Tsuruta et al. . |
| 5,389,103 | 2/1995 | Melzer et al. . |
| 5,395,367 | 3/1995 | Wilk . |
| 5,397,325 | 3/1995 | Della Badia et al. . |
| 5,403,328 | 4/1995 | Shallman . |
| 5,403,329 | 4/1995 | Hinchcliffe . |
| 5,437,681 | 8/1995 | Meade et al. . |
| 5,454,823 | 10/1995 | Richardson et al. . |
| 5,462,561 | 10/1995 | Voda . |
| 5,462,562 | 10/1995 | Elkus . |
| 5,468,251 | 11/1995 | Buelna . |
| 5,470,338 | 11/1995 | Whitfield et al. . |
| 5,474,057 | 12/1995 | Mackower et al. . |
| 5,474,568 | 12/1995 | Scott . |
| 5,477,794 | 12/1995 | Klundt . |
| 5,478,344 | 12/1995 | Stone et al. . |
| 5,478,345 | 12/1995 | Stone et al. . |
| 5,480,406 | 1/1996 | Nolan et al. . |
| 5,496,310 | 3/1996 | Exconde et al. . |
| 5,496,334 | 3/1996 | Klundt et al. . |
| 5,503,634 | 4/1996 | Christy . |
| 5,520,703 | 5/1996 | Essig et al. . |
| 5,540,704 | 7/1996 | Gordon et al. . |
| 5,540,705 | 7/1996 | Meade et al. . |
| 5,545,148 | 8/1996 | Wurster . |
| 5,562,640 | 10/1996 | McCabe et al. . |
| 5,562,685 | 10/1996 | Mollenauer et al. . |
| 5,562,686 | 10/1996 | Sauer et al. . |
| 5,562,703 | 10/1996 | Desai . |
| 5,569,164 | 10/1996 | Lurz . |
| 5,569,269 | 10/1996 | Hart et al. . |
| 5,569,270 | 10/1996 | Weng . |
| 5,573,542 | 11/1996 | Stevens . |
| 5,578,048 | 11/1996 | Pasqualucci et al. . |
| 5,582,617 | 12/1996 | Klieman et al. . |
| 5,591,181 | 1/1997 | Stone et al. . |
| 5,601,575 | 2/1997 | Measamer et al. . |
| 5,603,718 | 2/1997 | Xu . |
| 5,607,435 | 3/1997 | Sachdeva et al. . |
| 5,609,601 | 3/1997 | Kolesa et al. . |
| 5,626,588 | 5/1997 | Sauer et al. . |
| 5,632,751 | 5/1997 | Piraka . |
| 5,632,752 | 5/1997 | Buelna . |
| 5,643,292 | 7/1997 | Hart . |
| 5,662,663 | 9/1997 | Shallman . |
| 5,674,230 | 10/1997 | Tovey et al. . |
| 5,702,407 | 12/1997 | Kaji . |
| 5,707,379 | 1/1998 | Fleenor et al. . |
| 5,709,693 | 1/1998 | Taylor . |
| 5,709,694 | 1/1998 | Greenberg et al. . |
| 5,713,908 | 2/1998 | Jameel et al. . |
| 5,722,990 | 3/1998 | Sugarbaker et al. . |
| 5,810,805 | 9/1998 | Sutcu et al. . |

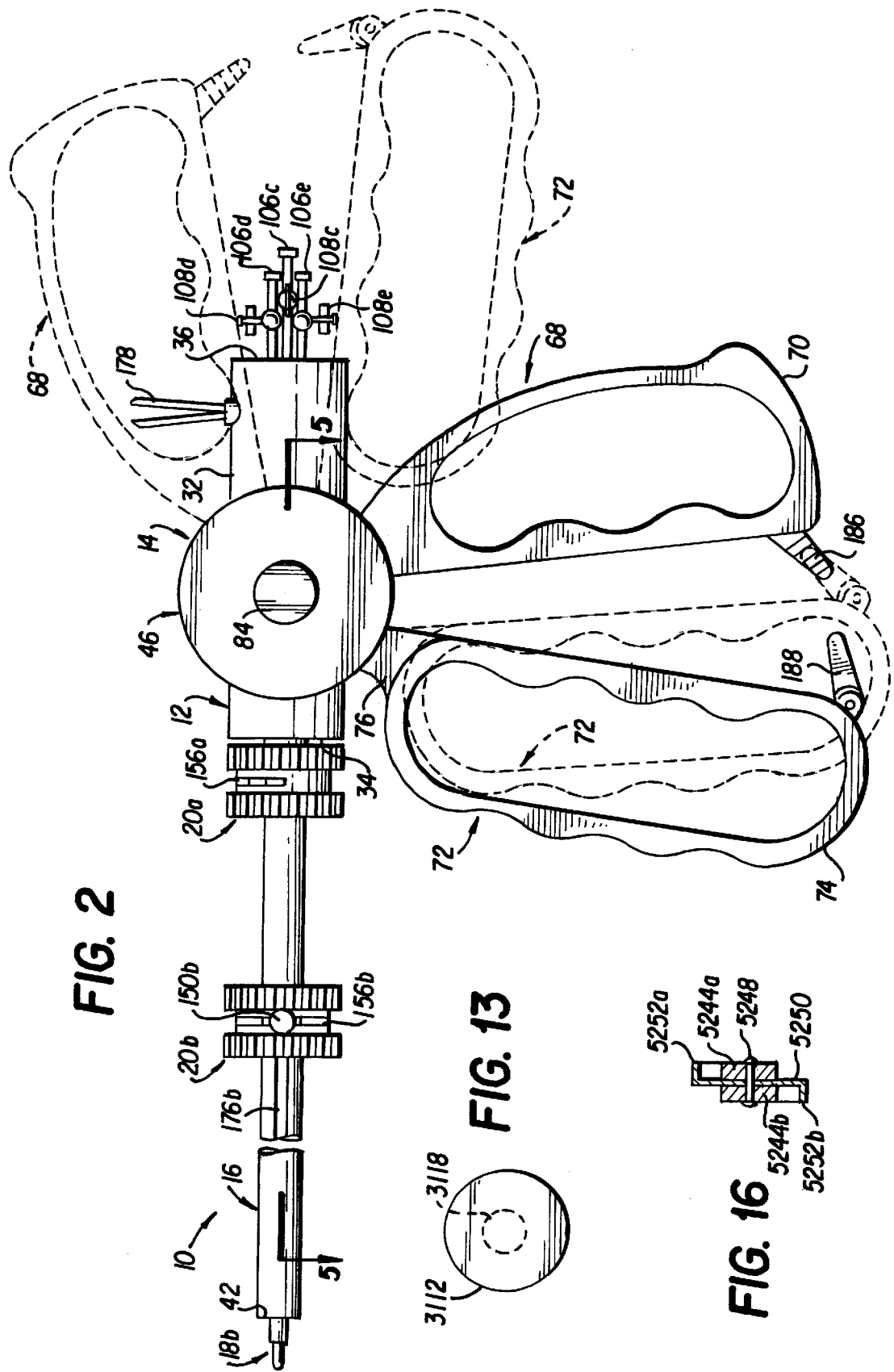

SURGICAL INSTRUMENT WITH MULTIPLE ROTATABLY MOUNTED SPREADABLE END EFFECTORS

BACKGROUND OF THE INVENTION

1. Field of the Invention

The present invention pertains to surgical instruments and procedures and, more particularly, to an instrument and method for performing various procedures during endoscopic and open surgery.

2. Discussion of the Related Art

Endoscopic and minimally invasive medical procedures, such as laparoscopy, have become widely accepted for surgery and diagnosis due to the associated advantages relating to reduced trauma and hospitalization time. The performance of an endoscopic procedure typically involves the creation of puncture sites through a wall of an anatomical cavity using penetrating instruments including an obturator, such as a trocar, disposed within a portal sleeve. After the penetrating instrument has penetrated into the anatomical cavity, the obturator is withdrawn leaving the sleeve in place to form a portal in the cavity wall through which endoscopes are introduced to view the surgical site and through which instruments having end effectors, such as forceps, cutters, needle holders, staplers, clip applicators and the like, are introduced at the surgical site. The end effectors are typically disposed at the distal end of the instrument and are manipulated by the surgeon using controls disposed at the proximal end of the instrument.

It is common in endoscopic procedures to use multiple end effectors in combination. However, typical endoscopic instruments include only one end effector, requiring several incisions for placement of multiple portal sleeves to accommodate a suitable number of endoscopic instruments for performing the required functions. Recently, however, in U.S. patent application Ser. No. 08/758,648, now U.S. Pat. No. 5,759,188; Ser. No. 08/847,182 and Ser. No. 08/877,764; it has been proposed to provide a plurality of end effectors on a single endoscopic instrument to minimize the number of puncture sites and thus reduce the risk and healing time associated with endoscopic surgery. The aforementioned patent applications disclose instruments having multiple needle holders movable with respect to one another to suture anatomical tissue; however, it would be desirable to incorporate other types of end effectors into a single endoscopic instrument so that the end effectors can be moved with respect to one another in a similar manner. Also, it would be desirable to move various types of end effectors through predetermined paths, such as an arc, to manipulate tissue without repositioning the entire endoscopic instrument. The needle holders described in the aforementioned patent applications can include distal portions that extend laterally outward at an angle from the instrument to provide a wide range of relative movement for suturing a wide range of tissue sizes. It would also be desirable to provide a wide range of relative movement between various types of end effectors to permit other operative acts or functions to be performed on a wide range of tissue sizes.

SUMMARY OF THE INVENTION

Accordingly, it is a primary object of the present invention to overcome the above-mentioned disadvantages of the prior art and to improve surgical instruments and methods of surgery including open and endoscopic surgery.

Another object of the present invention is to permit multiple end effectors to be used in combination in surgical procedures without the need of having to utilize multiple instruments.

Still another object of the present invention is to increase the working span or range of movement of multiple end effectors carried by a single instrument while minimizing the insertion diameter of the instrument.

An additional object of the present invention is to minimize the number of puncture sites required for performing operative steps on anatomical tissue in an endoscopic procedure by inserting more than one end effector through a single puncture site or incision with an instrument that is operable to move the end effectors relative to one another in a cooperative manner to operate on anatomical tissue.

The present invention is generally characterized in a surgical instrument including a housing, an elongate shaft having a proximal end mounted by the housing and a distal end with a peripheral edge, and first and second end effector assemblies protruding from the distal end of the elongate shaft. Each end effector assembly includes an end effector at a distal arm end. A distal portion of the first end effector assembly extends laterally outward at an angle from a first longitudinal axis of the elongate shaft to a position where at least a portion of the corresponding end effector is spaced laterally outward of the peripheral edge of the elongate shaft. In addition, the first end effector assembly is rotatable about the first longitudinal axis of the elongate shaft to cause the corresponding end effector to move along a first arcuate path having a center of curvature coaxial with the first longitudinal axis. In a preferred embodiment, the second end effector assembly is rotatable about the second longitudinal axis to cause the corresponding end effector to move along a second arcuate path having a center of curvature coaxial with the second longitudinal axis. The first and second end effector assemblies are also preferably movable from undeployed positions where the end effectors are spaced laterally inward of the peripheral edge of the shaft to deployed positions spaced laterally outward of the shaft, for example by rotation or axial movement relative to the shaft. The end effector assemblies are also preferably movable relative to one another in the axial or longitudinal direction.

Another aspect of the present invention is generally characterized in a surgical instrument for use in open and endoscopic procedures including a housing, an elongate shaft having a proximal end mounted by the housing and a distal end with a peripheral edge, and first and second end effector assemblies mounted by the shaft. The first end effector assembly includes a proximal portion extending at least part way through the elongate shaft along a first longitudinal axis, a distal portion extending laterally outward from the proximal portion at an angle, and an end effector mounted on the distal portion. The proximal portion of the first end effector assembly is rotatably mounted within the elongate shaft to move the end effector of the first end effector assembly along a first arcuate path having a center of curvature coaxial with the first longitudinal axis. The second end effector assembly also includes a proximal portion extending at least part way through the elongate shaft along a second longitudinal axis laterally spaced from the first longitudinal axis, a distal portion extending laterally outward from the proximal portion at an angle, and an end effector mounted on the distal portion. The proximal portion of the second end effector assembly is rotatably mounted within the elongate shaft to move the end effector of the second end effector assembly along a second arcuate path having a center of curvature coaxial with the second longitudinal axis. The first and second arcuate paths each preferably have a radius of curvature causing at least a portion of the end effector to extend outwardly of the peripheral edge of the elongate shaft.

Still another aspect of the present invention is generally characterized in a method of performing a surgical procedure in an anatomical cavity including the steps of introducing a surgical instrument having an elongate shaft into the anatomical cavity, the surgical instrument including first and second end effector assemblies protruding distally from the distal end of the elongate shaft, the first end effector assembly including a distal portion extending laterally outward at an angle from a first longitudinal axis of the elongate shaft to an end effector disposed at least partly outside a peripheral edge of the elongate shaft and the second end effector assembly including a distal portion extending laterally outward at an angle from a second longitudinal axis of the elongate shaft to an end effector disposed at least partly outside a peripheral edge of the elongate shaft, and operating on tissue within the anatomical cavity by rotating the first end effector assembly about the first longitudinal axis. Other operative steps or functions can be performed by moving the end effector assemblies axially relative to one another and by rotating the second end effector assembly about the first longitudinal axis.

Other objects and advantages of the present invention will become apparent from the following description of the preferred embodiments taken in conjunction with the accompanying drawings, wherein like parts in each of the several figures are identified by the same reference numerals or by reference numerals having the same last three digits.

BRIEF DESCRIPTION OF THE DRAWINGS

FIG. 2 is a side view, broken longitudinally, of the surgical instrument shown in FIG. 1.

FIGS. 12 and 13 are a fragmentary side view and a front view, respectively, of yet another modified end effector for use with the surgical instrument according to the present invention.

FIG. 16 is a cross-sectional view of the modified end effector of FIG. 15 taken through line 16—16.

DETAILED DESCRIPTION OF THE PREFERRED EMBODIMENTS

Figure 1:
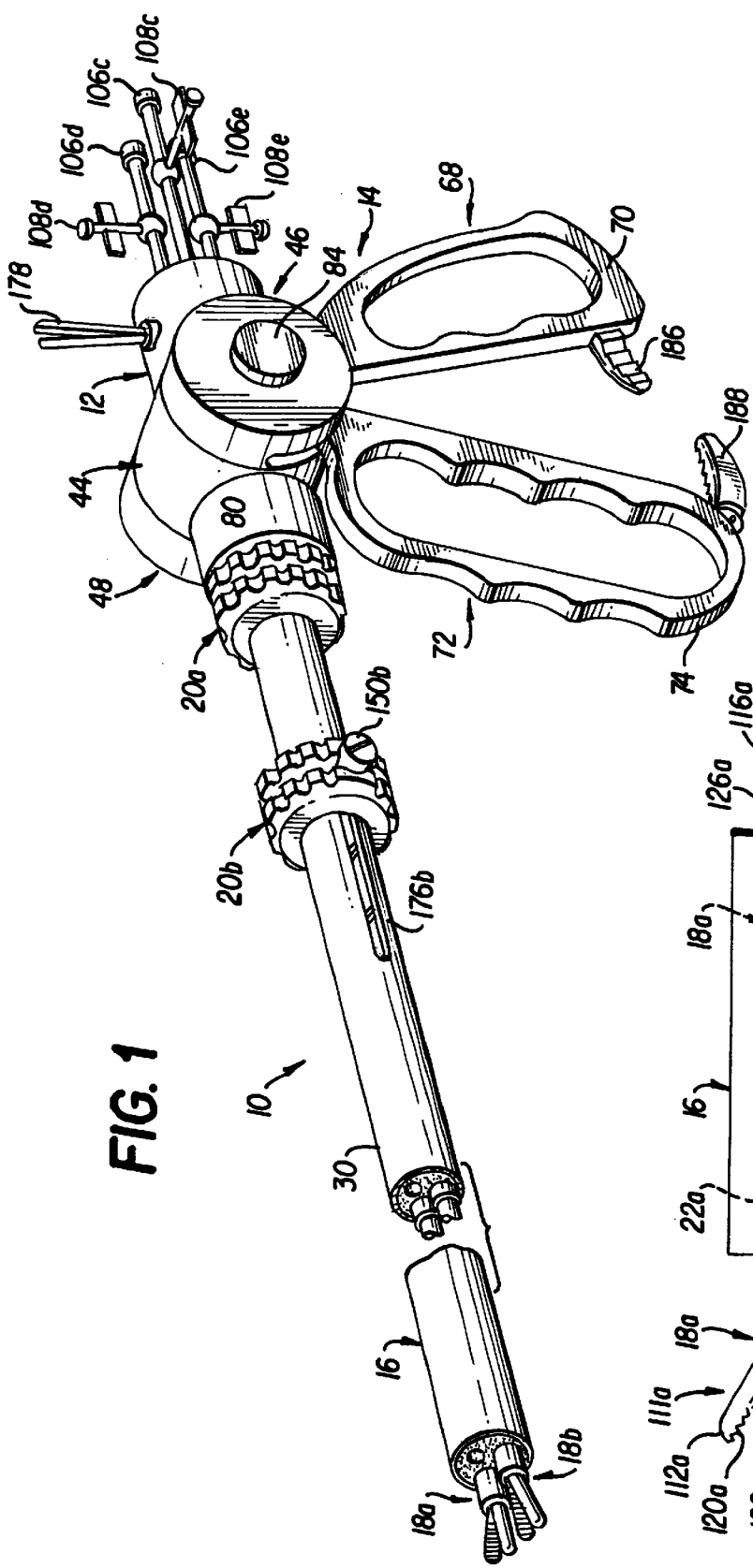
FIG. 1 is a perspective view, broken longitudinally, of a surgical instrument according to the present invention.

The surgical instrument of the present invention can be utilized to manipulate or otherwise operate on any type of anatomical tissue in any type of anatomical cavity; and, accordingly, while the instrument is described hereinafter for use with a portal sleeve in endoscopic procedures, such as laparoscopy, the instrument can be used in open surgery and with catheters and other small and large diameter tubular or hollow, cylindrical members providing access to small cavities, such as veins and arteries, as well as large cavities, such as the abdomen.

A surgical instrument 10 in accordance with the present invention, as illustrated in FIGS. 1–6, includes a hub or housing 12, a handle 14 coupled with the housing, an elongate shaft or barrel 16 extending distally from the housing, a pair of end effector assemblies 18a and 18b movably disposed within longitudinal channels formed through the shaft, and a pair of collars 20a and 20b disposed distally of the housing at axially spaced locations along the length of the shaft to control operation of the end effectors in conjunction with the handle.

Figure 4:
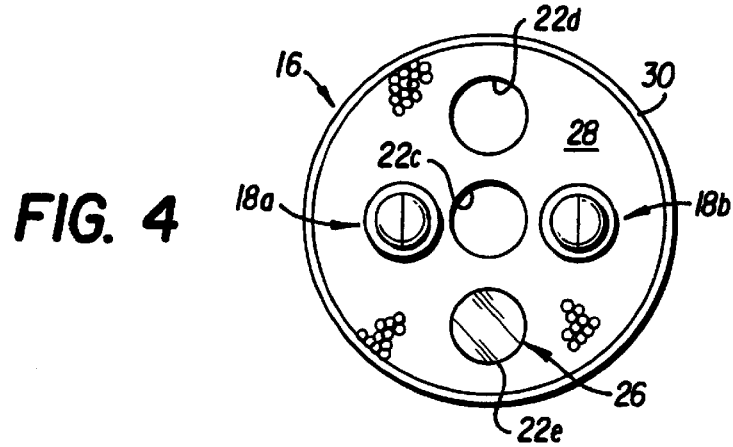
FIG. 4 is an enlarged front view of the distal end of the surgical instrument taken along line 4—4 in FIG. 3B.

As best seen in FIG. 4, elongate shaft 16 is of generally cylindrical configuration with a plurality of longitudinally extending passages or channels 22a, 22b, 22c, 22d and 22e defined therethrough in spaced, parallel relation, the channels each being of generally circular configuration in transverse cross-section. Channel 22c is disposed coaxial with a central longitudinal axis 24 of the shaft. Channels 22a and 22b are laterally offset from central channel 22c and are disposed on opposite sides of the central channel in diametrically opposed relation. Channels 22d and 22e are laterally offset from central channel 22c and are defined in the spaces between channels 22a and 22b. End effector assemblies 18a and 18b are shown extending through channels 22a and 22b, respectively, and an endoscope 26 of conventional design is shown extending through channel 22e. Channels 22c and 22d are shown in an open condition to provide access to an anatomical body cavity from outside the body via the surgical instrument without the need of having to create additional incisions or punctures through the wall of the anatomical cavity. Optical fibers 28 are shown extending through shaft 16 to transmit light from a proximal light source to the body cavity of the patient. The optical fibers are shown extending through a tubular member or sleeve 30 forming the outer surface of the shaft, however, the shaft can be formed without a separate sleeve, for example by embedding or molding the optical fibers within a medically acceptable polymer matrix or by adhesively connecting the fibers together. Channels 22a, 22b, 22c, 22d and 22e can optionally be formed by thin wall, tubular sleeves extending longitudinally through shaft 16 or by voids or spaces defined between the optical fibers as shown.

Figure 5:
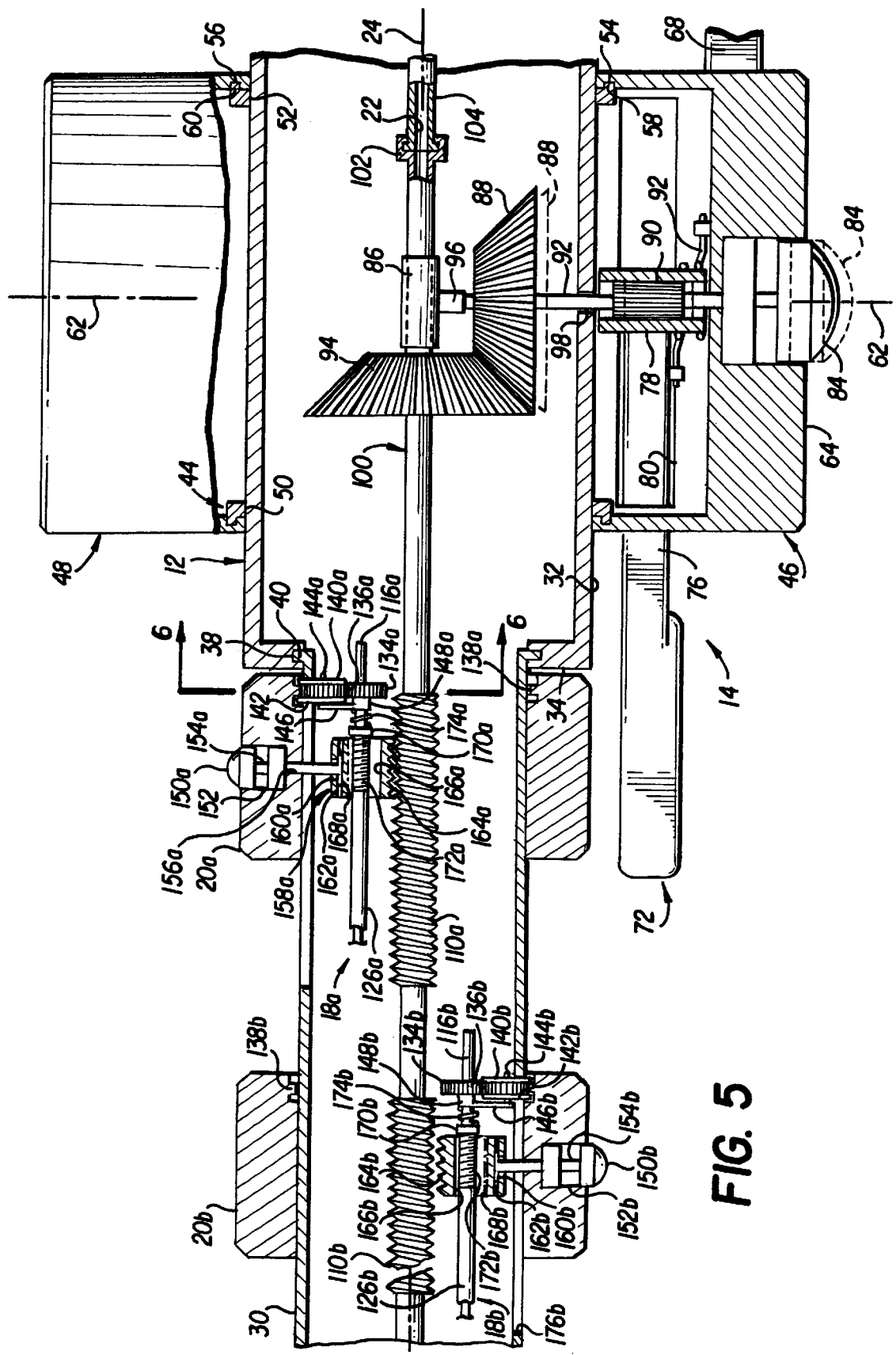
FIG. 5 is a fragmentary top view, partly in section, taken through line 5—5 in FIG. 2.
Figure 6:
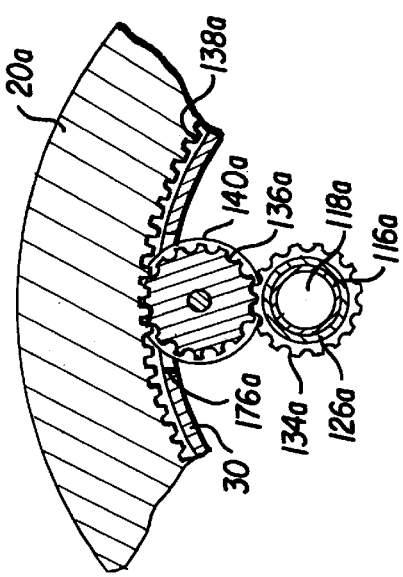
FIG. 6 is a fragmentary cross-sectional view of an end effector rotating mechanism for use with the surgical instrument according to the present invention taken through line 6—6 in FIG. 5.

As best seen in FIGS. 2 and 5, housing 12 includes a hollow, cylindrical portion or side wall 32 with longitudinally spaced front and rear walls 34 and 36 oriented perpendicular to longitudinal axis 24 of the shaft. Tubular member 30 of the shaft extends distally from an outwardly extending flange 38 fixedly mounted within a recess 40 formed in the front wall of housing 12 to a distal end of generally blunt configuration which cooperates with respective distal ends of the optical fibers to define a generally flat surface or face 42 at a distal end of the shaft, the distal face being shown oriented substantially perpendicular to the longitudinal axis of the shaft for purposes of illustration.

Handle 14 includes a central portion 44 of generally cylindrical configuration oriented perpendicular to the longitudinal axis of shaft 16 and a pair of end caps or end portions 46 and 48 of generally cylindrical configuration disposed at opposite axial ends of the cylindrical central handle portion. Central handle portion 44 is of larger diameter than housing 12 and is provided with axially aligned openings or holes 50 and 52 on opposite sides thereof to permit the cylindrical housing to be inserted cross-wise through the cylindrical central handle portion as shown in FIG. 5. Round flanges 54 and 56 extend outwardly from opposite axial ends of the central handle portion and are received within annular grooves 58 and 60 formed along inner surfaces of the cylindrical end caps 46 and 48 adjacent respective open ends of the end caps to permit rotation of the end caps about a central longitudinal axis 62 of handle portion 44. End caps 46 and 48 are of cup-like configuration and extend outwardly from respective open inner ends to outer ends closed by walls 64 and 66, respectively, of generally circular configuration oriented perpendicular to the longitudinal axis 62 of the central handle portion.

A fixed handle member 68 in the form of a finger loop 70 extends downwardly, looking at FIGS. 1 and 2, from the cylindrical side wall of end cap 46 at an acute angle relative to the proximal direction to accommodate one or more fingers of a user's hand. A movable handle member 72 includes a finger loop 74 disposed distally of fixed finger loop 70 and an arm 76 extending upwardly from the finger loop to a terminal end in the form of an internally splined sleeve or collar 78 of generally cylindrical configuration disposed within end cap 46 via an elongate slot 80 formed part way about the circumference of the cylindrical side wall of the end cap adjacent the point of attachment for finger loop 70. A transverse shaft 82 extends through splined sleeve 78 from a push button 84 disposed within a cylindrical recess formed in end cap wall 64 to a tubular sleeve or collar 86 with a smooth bore disposed within housing 12 perpendicular to the shaft. Transverse shaft 82 carries a bevel gear 88 of decreasing diameter in the direction of sleeve 86, the bevel gear being disposed between the smooth bore sleeve and the side wall of the housing. A spur gear 90 is carried on transverse shaft 82 within end cap 46. Spur gear 90 engages straight teeth or splines formed on an inner surface of sleeve 78 parallel to longitudinal axis 62 of the handle so that, among other things, pivotal movement of movable handle member 72 is translated into rotary movement of shaft 82. The movable handle member is preferably biased to move in a counterclockwise direction, looking at FIG. 2, toward fixed handle member 68, for example using a bias member 92 connected between the movable handle member and end cap 46. While a bias member in the form of a torsion spring is shown coiled around sleeve 78 in FIG. 5, it will be appreciated that other types of bias members can be used including, but not limited to, compression or expansion springs, leaf springs, rubber or magnets. Alternatively, the movable handle can be biased away from the fixed handle or configured for ratcheting or frictional movement.

Push button 84 is of a conventional type which, when pressed, alternatingly moves shaft 82 in the axial direction, along longitudinal axis 62 of the handle, between an engaged or depressed position where the first bevel gear 88 engages a second bevel gear 94 as shown by solid lines in FIG. 5 and a disengaged or elevated position, outwardly spaced from the extended position, where the first bevel gear is disengaged from the second bevel gear as shown by broken lines in FIG. 5. Spur gear 90 is disposed within end cap 46 and is of sufficient axial length to permit movement of the shaft in the axial direction while remaining at least partly engaged with splined sleeve 78 at the end of handle member 72. A tubular extension 96 extends radially outward from the smooth bored sleeve in the direction of bevel gear 88 to receive the inner terminal end of shaft 82 telescopically, the tubular extension being sufficiently long to accommodate axial movement of the shaft associated with operation of button 84. Shaft 82 extends through an elongate slot 98 formed part way about the circumference of housing sidewall 32 to permit rotation of handle 14 about the longitudinal axis of housing 12 as described in greater detail below.

Referring still to FIG. 5, second bevel gear 94 is mounted on an elongate drive shaft 100 extending longitudinally through the surgical instrument and is of decreasing diameter in the proximal direction to mesh with first bevel gear 88 when push button 84 is depressed or operated to move the first bevel gear to the engaged position. Drive shaft 100 is of hollow, tubular configuration and is oriented coaxial with longitudinal axis 24 of the surgical instrument to define central channel 22c. The drive shaft extends through smooth bored sleeve 86 to define an axis of rotation for the handle and terminates proximally at a rotational coupling 102 within housing 12 where the drive shaft connects telescopically with a tubular shaft extension 104, the tubular shaft extension preferably being fixed relative to a wall or walls of the housing so that it does not rotate or otherwise move with the drive shaft. Shaft extension 104 extends proximally from coupling 102 through housing rear wall 36 to a coupling 106, for example a Luer-type lock, for connection with sources of fluid or suction, operating units, or medical instruments and devices, with a valve 108 being disposed between the couplings to control passage of fluids and instruments through the central channel. The drive shaft is preferably formed of a medically acceptable plastic or metal material having a wall thickness sufficient to carry or form external threads at axially spaced locations within shaft 16 as shown at 110a and 110b in FIG. 5. As will be described in greater detail below, end effector assemblies 18a and 18b are coupled with threaded portions 110a and 110b of the drive shaft such that handle members 68 and 72 can be used to control operation of end effectors at respective distal ends of the end effector assemblies.

End effector assembly 18a and end effector assembly 18b each include an end effector in the form of a forceps mounted by the housing for rotation. While the end effectors are shown herein as forceps, it will be appreciated that any type of end effector can be used including, but not limited to, cauterizing electrodes, needle holders, dissectors, clip applicators, staplers, scissors, cutting members such as blades, needles, and biopsy devices.

Figure 3A:
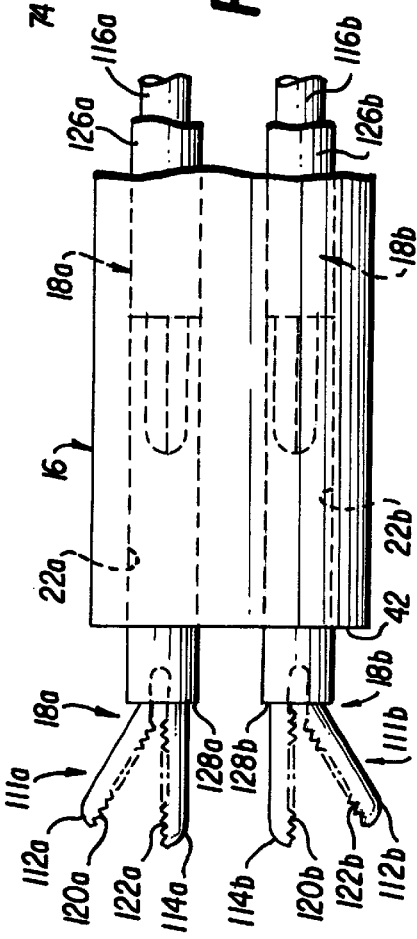
FIG. 3A is a fragmentary top view of the distal end of the surgical instrument shown in FIG. 2 with a pair of end effectors in axially retracted, open positions.
Figure 3B:
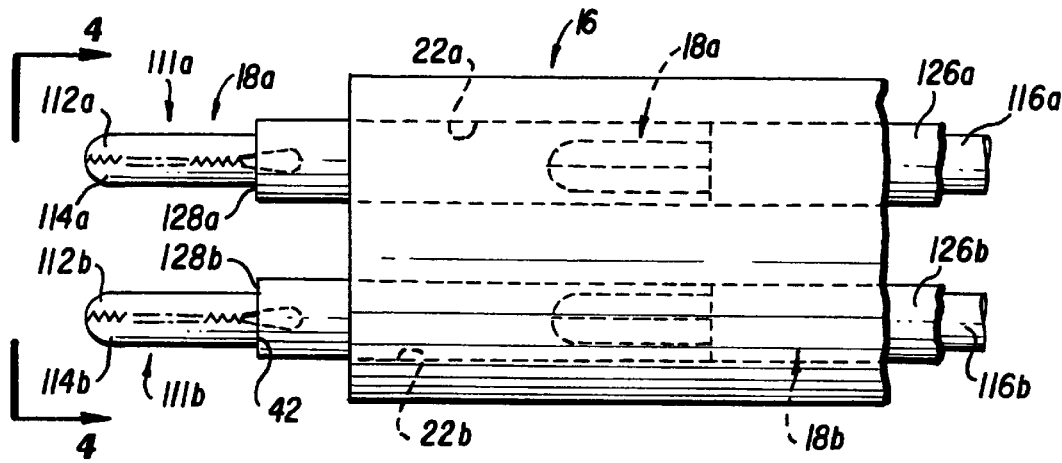
FIG. 3B is a fragmentary top view of the distal end of the surgical instrument shown in FIG. 2 with the end effectors in axially retracted, closed positions.

The end effector 111a of assembly 18a is shown in FIGS. 3A and 3B as a forceps having a pair of pivotally opposed jaws 112a and 114a. Jaws 112a and 114a are preferably formed at the distal end of an elongate tubular rod or body 116a as an integral one-piece unit; however, it will be appreciated that the jaws can be formed separately from the tubular rod and attached thereto and that the tubular rod can be of solid configuration in cross section, if desired. As shown, however, the tubular end effector rod 116a defines an elongate passage 118a through the end effector assembly which can be used as an additional or auxiliary operating channel providing access to the operative site from outside the body. Preferably, the tubular end effector rod 116a will terminate proximally at a coupling (not shown) similar to coupling 106 and will be provided with a valve (not shown) disposed distally of the coupling to control access through the operating channel 118a of the end effector assembly. The jaws of the end effector assembly are preferably biased apart toward an open position, shown in FIG. 3A, where inner needle holding or grasping surfaces 120a and 122a are angularly spaced from one another. The lower jaw 114a in FIG. 3A is of fixed configuration and extends in parallel with a longitudinal axis 124a at the distal portion of the end effector assembly while the upper jaw 112a is pivotally movable between an open position, shown in FIG. 3A, where it extends outwardly from the longitudinal axis 124a of the end effector assembly distal portion at an angle and a closed position, shown in FIG. 3B, where it is in substantially parallel, abutting relation with the lower jaw. Opposed inner surfaces 120a and 122a of the jaws are shown with a plurality of longitudinally spaced teeth or ribs oriented perpendicular to the longitudinal axis 124a of the end effector assembly distal portion to securely hold a suture needle, tissue or other objects therebetween during a surgical procedure; however, the inner surfaces can have any other suitable configuration for holding a suture needle and/or performing other functions including, but not limited to, configurations made up of spaced diamond-shaped protrusions, irregularly spaced teeth or ribs, opposed arcuate portions which define a hole or opening when closed, and transverse or longitudinal grooves. As will be described in greater detail below, either jaw can carry a cutting member or biopsy box.

Referring to FIGS. 3A, 3B and 4, it can be seen that fixed jaw 114a of the end effector assembly 18a is disposed between movable jaw 112a and central channel 22c so that, when the jaws of the end effector assemblies are in their respective open positions, the movable jaws will not contact one another or otherwise interfere with the movement of the other end effector. Under certain circumstances, however, it may be desirable to orient one or both of the end effector assemblies in a manner causing the movable jaw to be disposed inwardly of the fixed jaw, for example, by rotating the jaws 180° from the positions shown in FIG. 4. The tubular body or rod 116a of end effector assembly 18a is disposed telescopically within a flexible elongate outer member or sleeve 126a of tubular configuration which is axially movable relative to the rod between a retracted position, shown in FIG. 3A, where a distal end 128a of the flexible sleeve is proximally spaced from the jaws to allow them to open under the force of their own resilience and an extended position, shown in FIG. 3B, where the distal end of the flexible outer member slides over the jaws to cause them to close. The rod 116a and sleeve 126a of the end effector assembly cooperate to define an elongate proximal portion 130a of generally straight configuration extending through channel 22a in shaft 16 and a distal portion 132a with a predetermined deployed or working shape or condition where the distal portion bends outwardly at an angle relative to the longitudinal axis 125a of the proximal portion of the end effector assembly, the distal portion assuming the deployed shape or condition when the end effector assembly is in an axially extended position with the distal portion protruding distally beyond the distal end or face 42 of the shaft as shown, for example, in FIGS. 7 and 8. The length and angular deflection of the distal portion of the end effector assembly are such that at least portions of jaws 112a and 114a are spaced laterally outward of a peripheral edge or diameter of the shaft 16 when the distal portion of the rod is in the deployed condition. The tubular rod is preferably stiffer than the sleeve but formed of an elastic material or with an elastic portion having elastic properties allowing the distal portion to bend inwardly, in a lateral direction relative to the longitudinal axis of the proximal portion of the rod so that, when the rod is axially retracted or moved proximally relative to the shaft, the distal portion will move laterally inward from the deployed working position shown in FIGS. 7 and 8 to the undeployed insertion position shown in FIGS. 1 and 2. In the axially retracted position, a sufficient amount of the distal portion of the end effector assembly is disposed within the shaft to cause the distal portion to straighten out or assume an undeployed shape or condition where the jaws do not protrude beyond the outer periphery or diameter of the shaft. If desired, however, the instrument can be modified to permit complete retraction of the end effector assembly (and/or the end effector assembly) to a position where the jaws are proximally spaced from the distal end or face of the shaft as shown, for example, by broken lines in FIGS. 3A and 3B. Alternatively, a rigid outer sleeve (not shown) can be telescopically fitted around the end effector sleeve and moved axially or longitudinally along the end effector assembly to cause the distal portion to alternately straighten and spread laterally outward without the need of having to retract the entire end effector assembly into the instrument.

Tubular rod 116a of end effector assembly 18a carries a spur gear 134a adjacent a proximal end of collar 20a, the spur gear having straight teeth oriented parallel to longitudinal axis 125a of the proximal portion of the end effector assembly. An idler gear 136a is disposed between spur gear 134a and a sun gear 138a of epicyclic configuration formed along an inner surface of collar 20a adjacent the proximal end of the collar. Idler gear 136a includes a pair of face plates 140a and 142a of circular configuration which extend radially beyond the gear teeth to define a pair of lips or rims between which the spur gear and the epicyclic collar gear are disposed in order to maintain alignment of the gear system. Idler gear 136a is mounted on a pin 144a secured to a plate 146a extending upwardly, looking at FIG. 5, from the distal end of a tubular spacer 148a disposed telescopically around rod 116a adjacent spur gear 134a.

A push button 150a is disposed within a cylindrical recess 152a formed in an outer surface of collar 20a and includes a plunger or post 154a extending from the button through an elongate slot 156a formed part way about the circumference of the collar to a linear coupling block 158a disposed within shaft 16. Plunger 154a extends through a longitudinal slot 160a formed in block 158a to a cross member 162a wider than the slot so as to allow the block to slide transversely relative to the plunger while remaining attached to the plunger. Block 158a carries one or more external teeth 164a on a side facing threaded portion 110a of drive shaft 100 and defines a longitudinal opening or passage 166a therethrough with internal teeth 168a formed on an upper surface thereof looking at FIG. 5. The block is movable by operation of the button between an engaged position where teeth 164a meshingly engage threaded portion 110a of the drive shaft to cause the block to move linearly in response to rotation of the shaft and a disengaged position where the teeth 164a are radially or laterally spaced from the threaded portion such that the block is not moved in response to rotation of the shaft.

The tubular sleeve 126a of end effector assembly 18a extends through opening 166a in block 158a with lateral clearance and includes a round flange 170a extending radially outward therefrom between the block and spacer 148a and a rack made up of axially spaced rings or teeth 172a that extend around the portion of the sleeve disposed within the longitudinal block opening. Teeth 172a of the rack meshingly engage teeth 168a on the inner surface of the block opening when block 158a is in the engaged position shown in FIG. 5 such that axial movement of the block caused by rotation of shaft 100 is imparted to end effector assembly sleeve 126a thereby controlling the operation of jaws 112a and 114a as will be described in greater detail below.

A bias member 174a is disposed between spacer 148a and flange 170a to bias sleeve 126a distally relative to rod 116a so that jaws 112a and 114a are normally in a closed position. The bias member is shown as a helical spring coiled around rod 116a and held in compression between flange 170a and spacer 148a, however, any suitable bias member can be used including, but not limited to, tension springs, compression springs, helical springs, leaf springs, rubber and magnets.

End effector assembly 18b is shown as being identical to end effector assembly 18a, with an end effector 111b in the form of opposed jaws 112b and 114b mounted at the distal end of a tubular rod 116b slidably disposed within a sleeve 126b to define straight and angled portions 130b and 132b of the end effector assembly. It will be appreciated, however, that end effector 111b can have any useful configuration for performing surgical procedures. Tubular rod 116b of end effector assembly 18b carries a spur gear 134b engaging an idler gear 136b disposed between the spur gear and a sun gear 138b formed about the inner circumference of collar 20b. The gears are substantially the same as those described for end effector assembly 18a, with the idler gear being mounted on a pin 144b secured to a plate 146b extending radially or laterally outward from a tubular spacer 148b fitted telescopically around tubular rod 116b. Push button 150b, which controls engagement of a linear coupling block 158b with threaded portion 110b of drive shaft 100, is similar to push button 150a with a plunger or post 154b extending therefrom through a slot 156b extending part way about the circumference of collar 160b and a longitudinal slot 160b formed in coupling block 158b to a cross member 162b slidably disposed within the block. Like coupling block 158a for end effector assembly 18a, coupling block 158b carries external teeth 164b on a side facing a threaded portion of the drive shaft and defines a longitudinal passage or opening 166b therethrough through which sleeve 126b of the end effector assembly extends. Opening 166b includes teeth 166b on an inner surface thereof for engaging ring-like teeth 172b on the end effector assembly sleeve. Like the jaws of end effector assembly 18a, the jaws of end effector assembly 18b are biased to a closed position by providing a bias member 174b between a flange 170b carried by the sleeve and spacer 148b. As best seen in FIG. 5, idler gears 136a and 136b as well as plungers 154a and 154b extend through longitudinal slots 176a and 176b formed through tubular member 30 of the shaft on diametrically opposed sides of the shaft to permit axial movement of the collar assemblies when push buttons 150a and 150b are operated to move blocks 158a and 158b to disengaged positions such as the position of block 158b shown in FIG. 5. Preferably, collars 20a and 20b will slide frictionally against or be coupled in ratching relation to shaft 16 so that, once the collars are moved to a desired axial location relative to the shaft, the collars will not move unless deliberately forced. If desired, a separate locking mechanism can be provided for each collar to maintain the axial and/or angular location of the collar relative to the shaft.

An electrical connector can optionally be mounted on the housing 12, as shown at 178 in FIG. 1, or at any other suitable location on the instrument including, but not limited to, the instrument handle or the proximal end of one of the channel-defining tubular shafts extending proximally from the housing, to connect electrically conductive elements of the instrument with a source of electricity for performing unipolar or bipolar procedures such as electric coagulation, for example using one or both of the jaws of an end effector assembly as conductive elements. In addition, an interior surface of any of the channels 22a–22e can be coated with an electrical and/or thermal insulating layer to permit safe insertion of electrical, thermal and/or other types of energy transmitting devices through the operating channels.

In use, instrument 10 is preferably grasped using finger loops 70 and 74 and, in the case of an endoscopic procedure, the instrument is guided to the operative site by a portal sleeve positioned in the wall of an anatomical cavity. The portal sleeve can be positioned in the anatomical cavity wall using any suitable penetrating technique, including those creating puncture sites by means of removable obturators, such as trocars, and can include a valve housing, if desired, to prevent loss of pneumoperitoneum during insertion and withdrawal of the instrument. The visualization of the endoscopic procedure can be accomplished using a conventional endoscope incorporated into the instrument, for example within the longitudinal operating channel 22e defined through shaft 16, or separately positioned within the anatomical cavity through a second portal sleeve located at another puncture site.

Prior to insertion, instrument 10 is preferably in the condition, state or position shown in FIGS. 3B and 4. More specifically, end effector assembly 18a and end effector assembly 18b are preferably initially in axially retracted positions where respective distal portions of the end effector assemblies are drawn at least part way into elongate shaft 16 and thus forced to move laterally inward in an elastic manner to undeployed positions where the end effector jaws are spaced laterally inward of the peripheral edge of the shaft so as not to snag or catch on structure within the portal sleeve or valve housing during insertion. To this end, collars 20a and 20b are preferably initially disposed in the retracted positions shown in FIG. 2 with plungers 154a and 154b being disposed at the proximal ends of slots 176a and 176b in the shaft. Alternatively, a sheath (not shown) can be telescopically fitted around the shaft in a manner to be movable axially or longitudinally between a retracted position spaced proximally of the end effectors and an extended position protruding distally from the shaft to cover and protect the end effectors. Push buttons 150a and 150b on collars 20a and 20b, respectively, are preferably initially disposed in elevated positions so that the jaws of both end effector assemblies will be in closed or grasping positions with inner grasping surfaces of the jaws close together or abutting one another.

Figure 7:
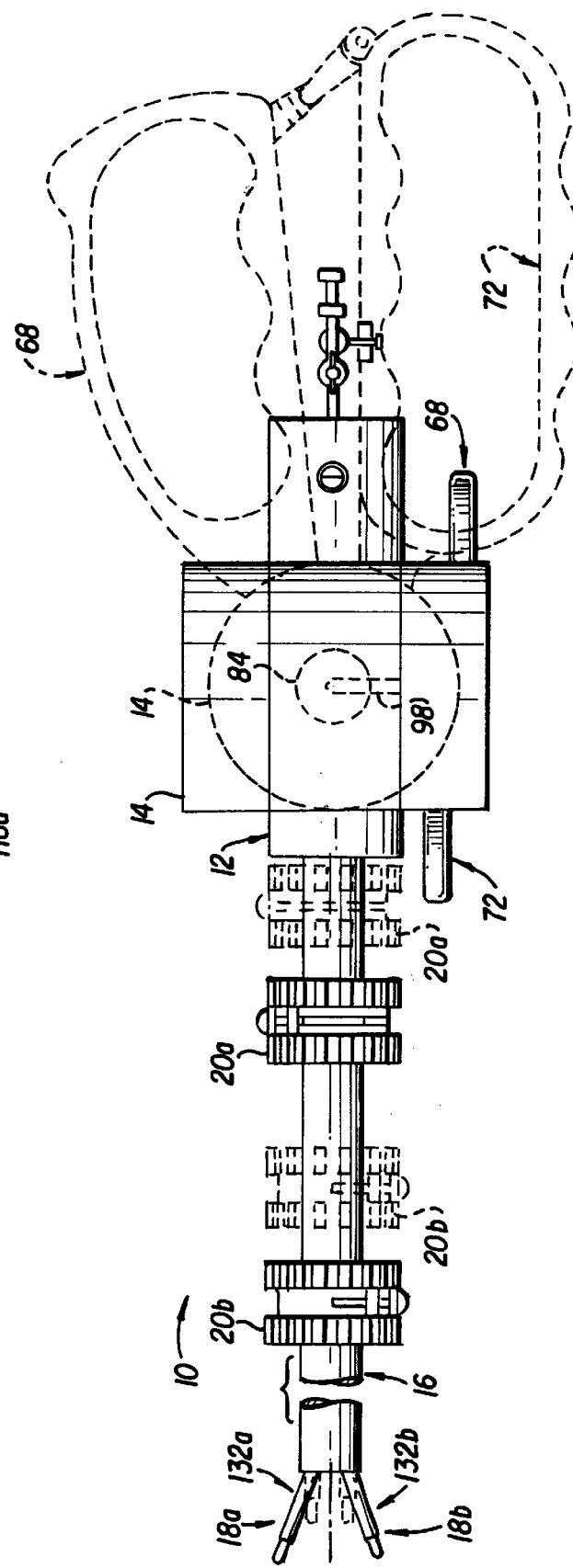
FIG. 7 is a top view, broken longitudinally, of the surgical instrument according to the present invention with the end effectors in axially extended, deployed positions.
Figure 7A:
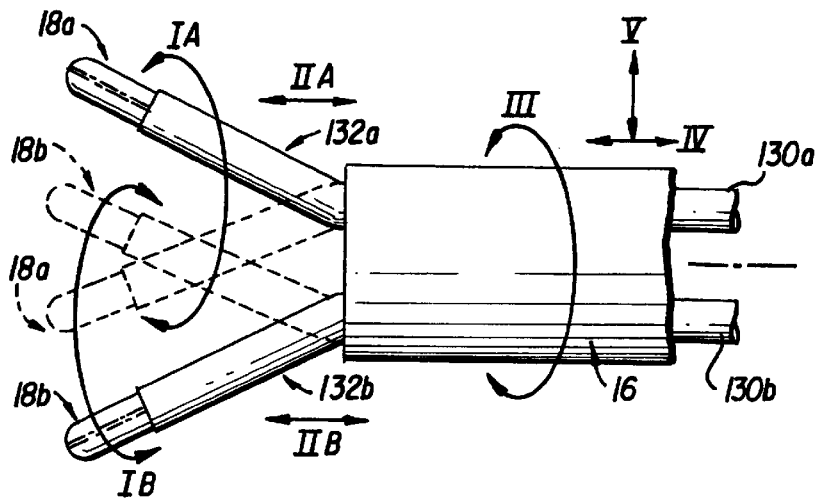
FIGS. 7A, 7B and 7C are fragmentary side views of the distal end of the surgical instrument illustrating use of the surgical instrument according to the present invention.

After insertion, end effector assembly 18a and end effector assembly 18b can be moved distally relative to shaft 16 from the axially retracted, undeployed positions shown in FIG. 3B to the axially extended, deployed positions shown by solid lines in FIGS. 7 and 7A by sliding collars 20a and 20b distally along longitudinal slots 176a and 176b. As the end effector assemblies are advanced longitudinally, distal portions of the end effector assemblies will no longer be restrained within the channels of the elongate shaft and will thus tend to recover elastically or move toward the undeformed shape or condition shown by solid lines in FIG. 7. More particularly, distal portions of the end effector assemblies will spread apart or bend outwardly, away from the longitudinal axes of the channels from which they extend, toward deployed positions where the jaws of each of the end effector assemblies are spaced laterally outward of the peripheral edge or outer diameter of the shaft.

Referring now to FIG. 7A, end effector assemblies 18a and 18b can be individually or simultaneously rotated about their respective longitudinal axes to produce movement of their respective end effectors along arcuate paths shown by arrows at IA and IB. Rotation of an end effector assembly in a first direction is accomplished by turning the corresponding collar in a second direction opposite the first direction, thereby causing the sun gear on the inner surface of the collar to rotate in the second direction. Rotation of the sun gear in the second direction causes the idler gear to rotate in the first direction, thereby causing the spur gear and, thus, the entire end effector assembly to rotate within the channel in the first direction. The end effector assemblies can also be individually or simultaneously moved proximally and distally along longitudinal paths indicated by arrows at IIA and IIB to cause the end effectors to move axially relative to one another and/or the shaft. As mentioned above, proximal and distal movement of an end effector assembly is accomplished by sliding the corresponding collar along the slots formed in the shaft, it being understood that proximal movement of the end effector assembly from the axially extended position to the axially retracted position can be accompanied by lateral movement of the distal portion of the end effector assembly toward the longitudinal axis of the assembly as the distal portion is drawn into a channel of the shaft. Such lateral movement can also be used to perform certain surgical procedures. In addition to the above, shaft 16 can be rotated about longitudinal axis 24 as indicated by the curved arrow at III, moved axially and distally along the directions shown by the arrow IV, and/or moved laterally in the directions shown by the arrow at V. It will be appreciated that any of the above movements can be combined where necessary or desirable to achieve a specific result. It is also possible for one of the end effector assemblies to remain stationary while the other end effector assembly is moved.

Figure 7B:
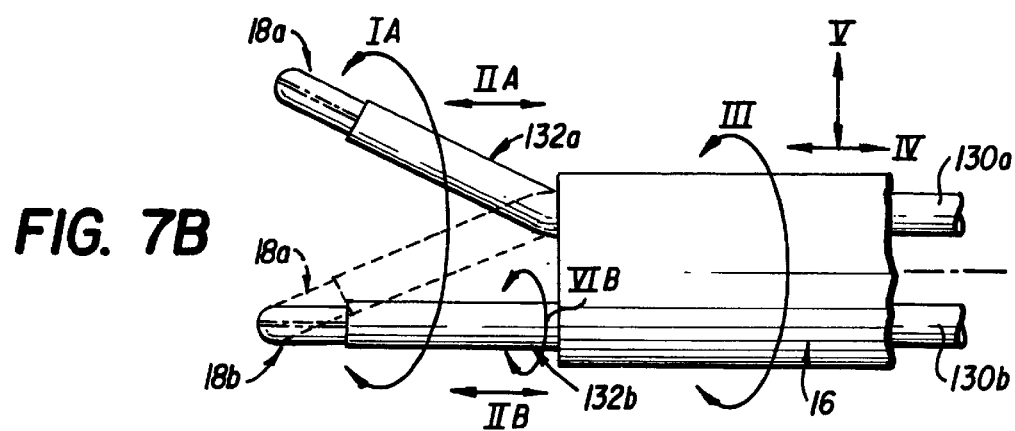

Under certain circumstances, it may be desirable for one of the end effector assemblies to bend outwardly in the extended position while the other end effector assembly remains within the periphery of the outer tubular member in the axially extended position, for example as shown in FIG. 7B. The spreadable end effector assembly 18a can be moved in any of the ways described above (i.e., in the directions indicted by arrows IA and IIA). The other end effector assembly 18b is either straight or only slightly bent or curved so that the end effector at the distal end of the non-spreadable end effector is not movable along an arcuate path. The end effector assembly 18b may, however, be rotated about its longitudinal axis in the direction indicated by the arrow at VIB and may be moved axially in the directions indicated by the arrow IIB. Shaft 16 can also be moved in any of the directions indicated by arrows III, IV or V.

Figure 7C:
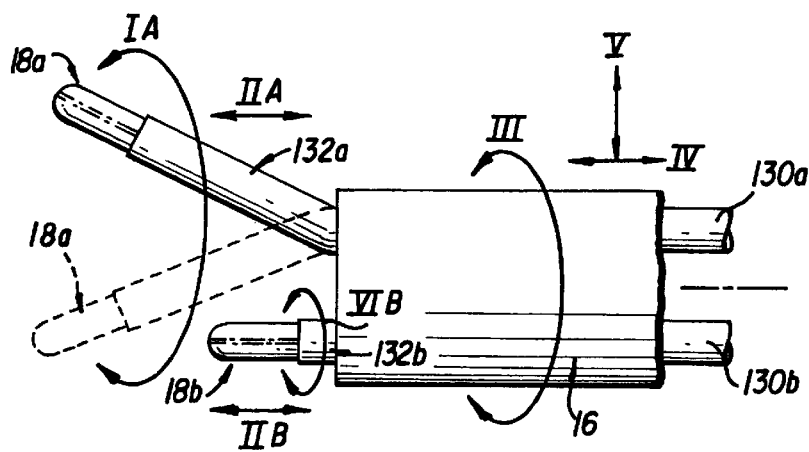

FIG. 7C shows one of the end effector assemblies bending outwardly in the extended position and the other end effector assembly in an axially retracted position where the end effector is disposed within the periphery of the elongate shaft. The end effector assembly 18a shown in the axially extended position can be moved in any of the ways described above (i.e., in the directions indicated by arrows IA and IIA). The other end effector assembly 18b can be relatively straight or bent like end effector assembly 18a in the axially extended position; however, when the end effector assembly 18b is in the axially retracted position shown in FIG. 7C, it may be rotated about its longitudinal axis in the direction indicated by the arrow at VIB or moved axially in the directions indicated by the arrow IIB. As mentioned above, shaft 16 can also be moved in any of the directions indicated by arrows III, IV or V.

Figure 8:
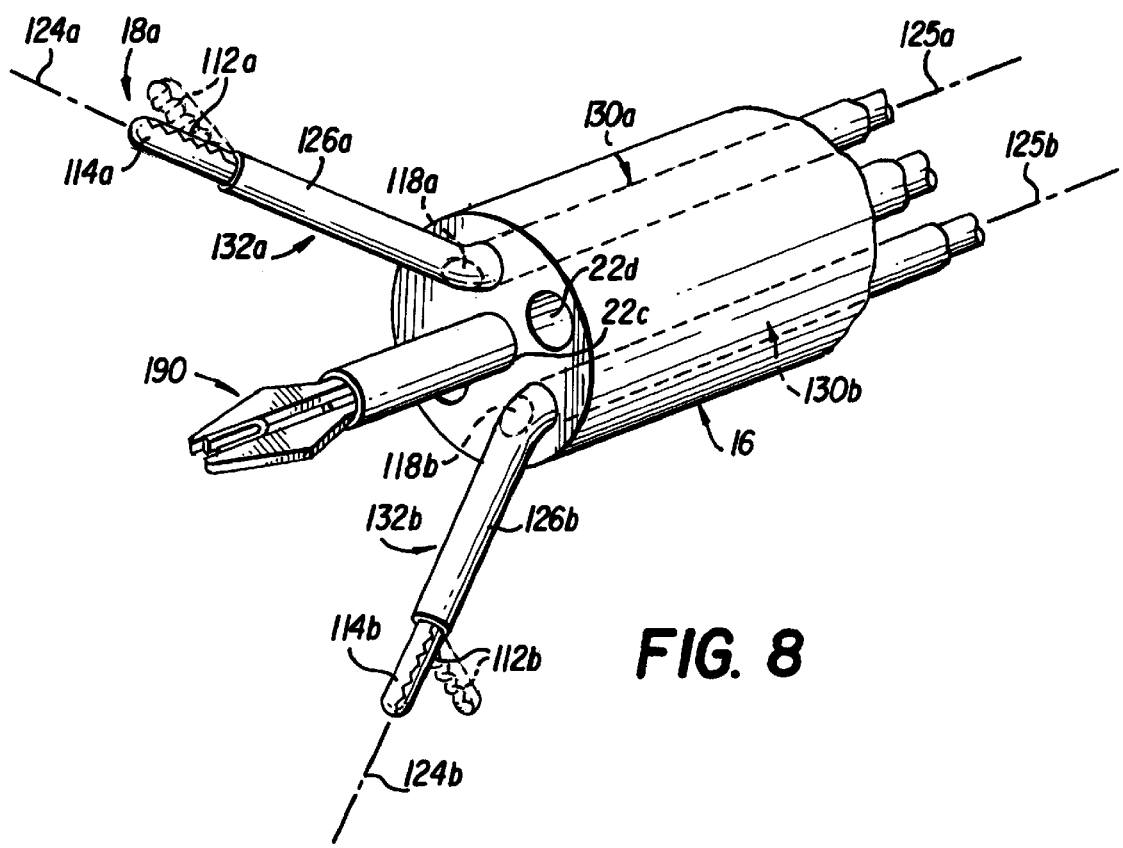
FIG. 8 is a fragmentary perspective view of the distal end of the surgical instrument shown in FIG. 7.

Referring to FIGS. 7 and 8, the jaws of each end effector assembly can be moved between the open position shown by broken lines and the closed position shown by solid lines by operation of handle members 68 and 72 of the instrument. If push button 84 of the handle is in the elevated or disengaged position shown by broken lines in FIG. 5, the push button is depressed to cause bevel gear 88 to move inwardly, in the direction of longitudinal axis 24, and into meshing engagement with bevel gear 94 mounted on drive shaft 100, as shown by solid lines in FIG. 5. To move the jaws from the open position to the closed position, movable handle member 72 is moved in a counterclockwise direction, looking at FIG. 2, toward fixed handle member 68 to cause internally threaded sleeve 78 to rotate in a counterclockwise direction. Spur gear 90 rotates with sleeve 78, causing shaft 82 to rotate in the counterclockwise direction with bevel gear 88. Bevel gear 94 meshingly engages bevel gear 88 and is thus rotated in a clockwise direction, looking proximally, in response to counterclockwise rotation of bevel gear 88 thereby causing drive shaft 100, including threaded portions 110a and 110b, to rotate in a clockwise direction. Rotation of the drive shaft 100 can be converted into linear movement of the end effector assembly components by selectively depressing one or both of the buttons 150a and 150b mounted on collars 20a and 20b. Depression of the buttons causes blocks 158a and 158b to move inwardly, toward the drive shaft, such that teeth 164a and 164b mesh with or engage the threaded portions 110a and 110b, respectively, of the drive shaft. Coupling blocks 158a and 158b move linearly in the distal direction along the drive shaft as the drive shaft rotates in the clockwise direction, with the plungers 154a and 154b sliding axially within the slots 160a and 160b formed through the blocks. In the depressed or engaged condition shown at the top of FIG. 5, the teeth or rings 172a of the end effector assembly sleeve 126a engage teeth 168a inside the block opening 166a such that the end effector assembly sleeve 126a moves linearly with the block in the distal direction relative to rod 116a. The distal end 128a of sleeve 126a is thus moved distally relative to the jaws, causing the jaws to come together or move toward the closed position shown in FIG. 3B against the force biasing the upper jaw away from the lower jaw. The jaws can be locked in a closed position by use of ratchet members 186 and 188 on opposed sides of finger loops 70 and 74; however, if it is not necessary or desirable for the finger loops to be locked together, one of the ratchet members may be pivoted to prevent engagement with the other ratchet member.

To open the jaws, movable handle member 72 is released or otherwise caused to move in a clockwise direction, looking at FIG. 2, in response to finger pressure and/or the spring bias provided by bias member 92. As the movable handle member 72 moves clockwise, transverse shaft 82 is also caused to move clockwise thereby carrying bevel gear 88 in the clockwise direction. Bevel gear 94 is thus caused to move in a counterclockwise direction, looking proximally along longitudinal axis 24, so that drive shaft 100 is driven counterclockwise, causing block 158a to move in the proximal direction relative to rod 116a such that distal end 128a of the sleeve moves proximally relative to the rod to allow jaws 112a and 114a to move resiliently apart.

Dependent upon the procedure to be performed, closing of the jaws may be used to grasp or hold an object positioned between the jaws. If the jaws are provided with a cutting member, objects positioned between the jaws can be cut when the jaws are closed. Similarly, if a biopsy box is mounted on the jaws, tissue samples may be taken from tissue positioned between the jaws when the jaws are closed. One or both of the jaws may also function as a cautery electrode, if desired. Conversely, opening of the jaws can be used to spread objects apart or to permit a suture needle, tissue or some other object to be placed between the jaws. The foregoing functions are merely exemplary of the types of functions that may be performed using an end effector assembly with an end effector in the form of jaws.

At any point during the surgical procedure, operating channels 22a–22e can be used for irrigation or aspiration of the surgical site and can serve as a space for holding objects or devices such as needles and suture material or as a portal for the introduction of other medical instruments and devices such as, for example, forceps, cutting members, staplers and endoscopes. Knotting elements can also be introduced at the operative site via the operating channels for use in leu of or in addition to traditional knotting techniques during suturing procedures. Some examples of suitable knotting elements for this purpose are described in pending applications Ser. Nos. 08/366,285, filed Dec. 29, 1994; 08/377,723, filed Jan. 25, 1995; 08/401,002, filed Mar. 9, 1995; and 08/585,875, filed Jan. 16,1996; the disclosures of which are incorporated herein by reference.

FIG. 8 illustrates a further use of one of the operating channels 22a–22e wherein a conventional clip applier 190 is advanced distally through one of the channels, for example central channel 22c, to apply a clip as part of a surgical procedure. End effector assemblies 18a and 18b are shown by solid lines in their axially extended, outwardly spread positions with jaws closed and by broken lines with their jaws open. The end effector assemblies can be used in any suitable manner to manipulate or position tissue so that it can be clipped or to move tissue so that the clip applier can access other areas of the body. In addition to operating channels 22a–22e, auxiliary operating channels can be defined through one or both of the end effector assemblies 18a and 18b as shown at 118a and 118b in FIGS. 3A and 3B to provide access to the operative site from outside the anatomical cavity. The auxiliary operating channels are shown terminating distally at openings adjacent the jaws of the end effector assemblies but can terminate at openings defined at the bend connecting straight and angled portions of the end effector assemblies as shown by broken lines in FIG. 8.

It will also be appreciated that when push button 84 is in the elevated, undepressed position shown by broken lines in FIG. 5, shaft 82 slides outwardly within tubular extension 96, moving bevel gear 88 away from bevel gear 94 so that end cap 46 may be rotated about an axis transverse to the longitudinal axis of shaft 16 to move handle members 68 and 72 between the transverse position shown by solid lines in FIG. 2 and the rearward facing position shown by broken lines in FIG. 2. Push button 84 may then be depressed to maintain the handle members in the desired angular orientation. The handle members 68 and 72 can also be rotated about the longitudinal axis of the shaft 16 (e.g., as shown by broken lines in FIG. 7) by moving push button 84 to the elevated, undepressed position and rotating the entire handle portion 14 about the housing 12, for example by grasping the housing with one hand while moving the handle with the other hand. When a desired angular orientation is achieved, push button 84 may be depressed so that the bevel gear 88 is made to engage bevel gear 94, thereby locking the handle in place relative to the housing.

Figure 10:
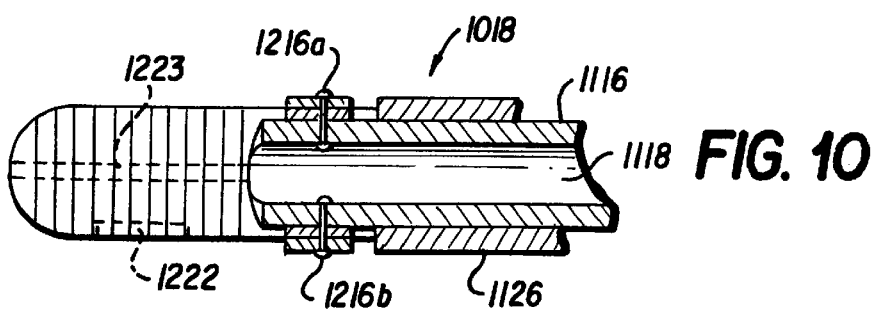
FIG. 10 is a cross-sectional view of the modified end effector of FIG. 9 taken through line 10—10.
Figure 9:
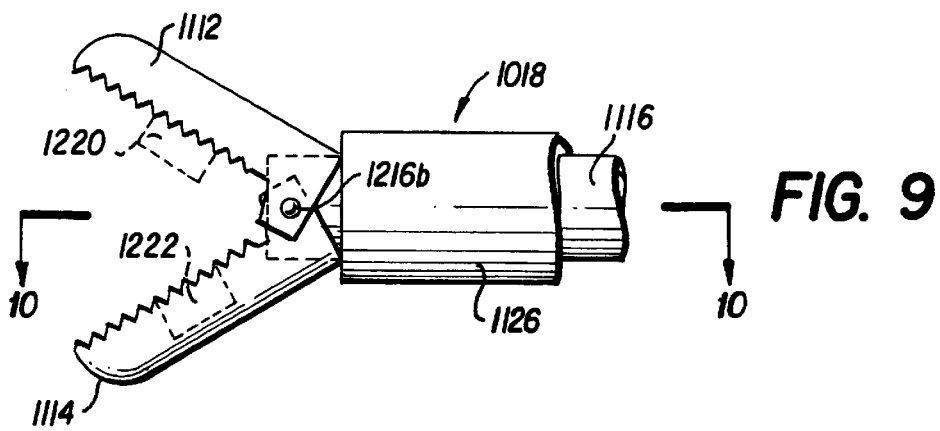
FIG. 9 is a fragmentary side view of a modified end effector for use with the surgical instrument according to the present invention.

FIGS. 9 and 10 show a modification of an end effector assembly for use with the surgical instrument according to the present invention wherein the modified end effector assembly 1018 includes a pair of jaws 1112 and 1114 pivotably mounted on a pair of pins 1216a and 1216b secured to diametrically opposed sides of a hollow tubular rod or sleeve 1116 telescopically fitted within an outer tubular sleeve 1126, the tubular rod defining an auxiliary operating channel 1118 providing access to the operative site from outside the anatomical cavity. Jaws 1112 and 1114 are biased apart toward the open position shown in FIG. 9, for example using a torsion spring (not shown) coiled around one of the pins and connected between the jaws or a pair of spring members (not shown) held in compression between each jaw and the hollow tubular rod, and the jaws are movable inwardly toward one another against the spring bias in response to distal movement of tubular sleeve 1126 against the rear or back edges of the jaws. If desired, jaws 1112 and 1114 can be mounted on a single pin or pivot extending diametrically across the width of sleeve 1116; however, use of separate pivots provides a substantially unobstructed passage through the operating channel.

Any of the end effector jaws described herein can carry a biopsy box or a cutting member such as the blade shown by broken lines at 1220 in FIG. 9. Blade 1220 is oriented perpendicular to the inner grasping surface of upper jaw 1112 and extends downwardly, looking at FIG. 9, from an edge of the inner grasping surface to fit within a cooperatively configured pocket or recess 1222 formed along an edge of lower jaw 1114 when the jaws are closed together. An elongate groove or recess with an open proximal end can be formed along an inner surface of one or both of the jaws, for example as shown by broken lines at 1223 in FIG. 10, to permit a cutting member, such as a blade, to slide between the jaws when closed. Other examples of cutting members which can be used are shown and described in U.S. patent application Ser. No. 08/612,634, filed Mar. 4, 1996, and U.S. patent application Ser. No. 08/376,186, filed Jan. 20, 1995, the disclosures of which are incorporated herein by reference.

Figure 11:
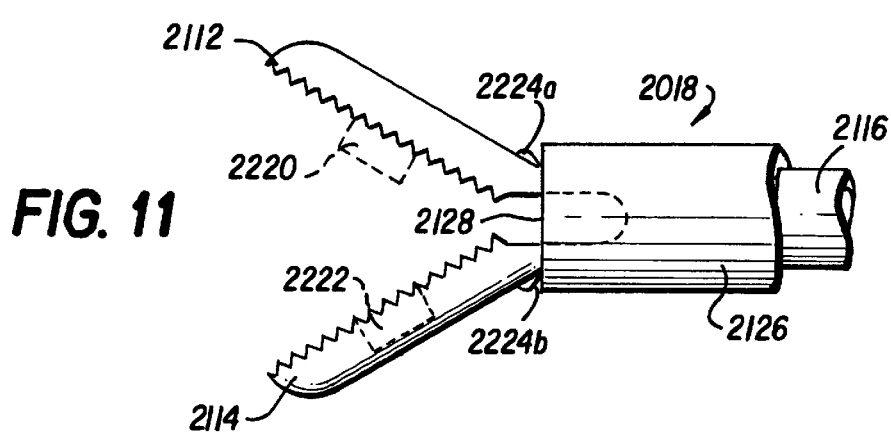
FIG. 11 is a fragmentary side view of another modification of an end effector for use with the surgical instrument according to the present invention.

The modified end effector assembly 2018 shown in FIG. 11 is similar to the end effector assemblies shown in FIGS. 1–8 but with both jaws 2112 and 2114 being pivotably movable between normally open positions extending laterally outward from the tubular rod 2116 at acute angles and closed positions wherein the jaws abut one another. A pair of cams 2224a and 2224b are also shown extending outwardly from the jaws adjacent the distal end 2128 of outer sleeve 2126 to provide additional force when closing the jaws together. An optional cutting member in the form of a blade 2220 and a cooperatively configured pocket or recess 2222 are also shown.

Figure 12:
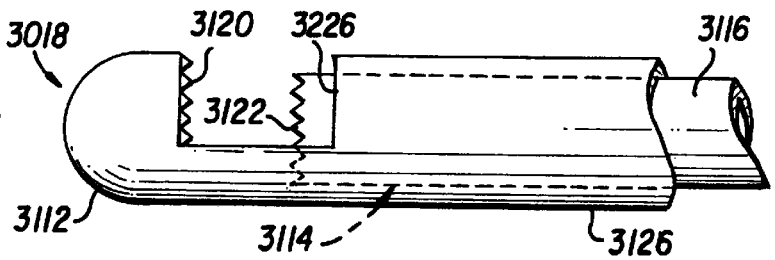

Yet another modified end effector assembly is shown in FIGS. 12 and 13 at 3018 and includes a first jaw member 3112 in the form of an outer tubular sleeve 3126 with a lateral cut-out or window 3226 having a grasping surface 3120 formed on a proximalfacing surface or face of the window and a second jaw member 3114 in the form of an inner tubular sleeve 3116 fitted telescopically within the outer tubular sleeve and having a grasping surface 3122 formed along a peripheral edge of the inner member to operate cooperatively with the grasping surface at the distal end of the outer member to hold a suture needle or other objects within the window. An auxiliary operating channel, shown by broken lines in FIG. 23 at 3118, may optionally be formed through the inner and outer members of the end effector assembly to permit access to the operative site via the channel from outside the body. If an auxiliary operating channel is not needed or desired, the second jaw member 3114 can be solid instead of tubular, thus presenting a wider grasping surface if desired.

Figure 14:
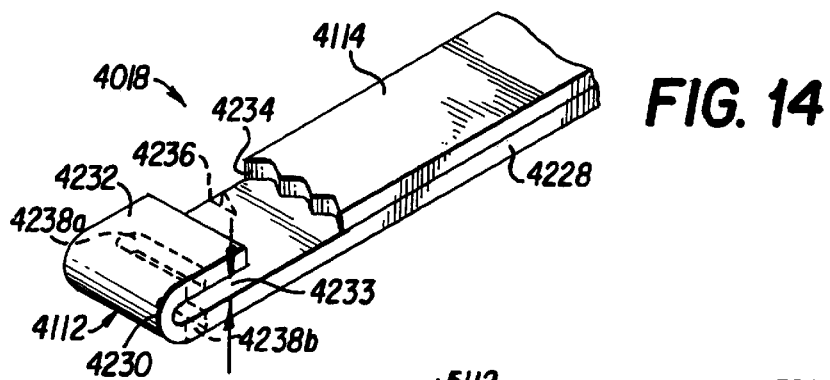
FIG. 14 is a fragmentary perspective view of still another modification of an end effector for use with a surgical instrument according to the present invention.

FIG. 14 shows still another modification of an end effector assembly for use with the surgical instrument according to the present invention wherein the modified end effector assembly 4018 includes a first needle holding member 4112 in the form of a hook and a second needle holding member 4114 in the form of a keeper movable relative to the hook to capture and release a suture needle placed within the hook. The needle holding members are preferably formed of flat strips of a medically acceptable material, such as stainless steel, configured to lay flat against one and other to permit relative sliding movement of the needle holding members. The first needle holding member 4112 includes an elongate portion or leg 4228 extending distally from within the instrument housing to a bend 4230 where the first needle holding member folds inwardly upon itself to form a short leg 4232 parallel to the elongate portion or leg of the needle holding member thereby defining a hook with a proximal-facing mouth 4233 having a gap width suitable for receiving the shaft or body of a suture needle. The second needle holding member 4114 is slidingly disposed along the first needle holding member 4112 and includes a distal end 4234 configured to fit within the mouth of the hook as a keeper, the distal end of the second needle holding member being shown with an optional scalloped edge having one or more curved recesses. The first or second needle holding member may also be formed with a cutting member such as a blade or a notch of generally V-shaped configuration defined along an edge of the needle holding member and having one or more sharp edges to cut lengths of suture material received therein under pressure as shown, for example, by broken lines at 4236 in FIG. 14. The first needle holding member is also shown with optional slots or openings 4238a and 4238b formed on opposite sides of the hook to permit straight or slightly curved suture needles to be placed perpendicularly through short and long legs of the hook so as to be oriented radially relative to the longitudinal axis of the shaft. The slotted openings extend transversely, relative to a longitudinal axis of the end effector assembly, from respective open ends disposed along a lateral or longitudinal edge of the first needle holding member to generally centrally located terminal tends of rounded or semi-circular configuration with a size to receive the body or shank of a suture needle extending transversely through legs of the hook. As mentioned above, the scalloped edge at the distal end of the second needle holding member or keeper 4114 is configured with laterally spaced recesses, one of which is preferably aligned with a terminal portion or end of the slotted openings to cradle a needle positioned within the openings.

Figure 15:
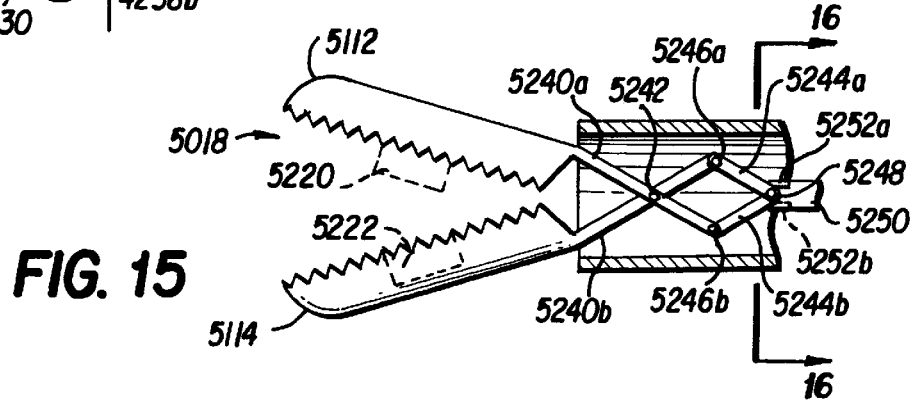
FIG. 15 is a fragmentary side view, partly in section, of yet another modification of an end effector for use with a surgical instrument according to the present invention.

Still another modification of an end effector assembly for use with the surgical instrument according to the present invention, as shown in FIGS. 15 and 16, includes a pair of jaws 5112 and 5114 extending distally from a pair of crossed arms 5240a and 5240b connected by a pivot 5242 located medially along the lengths of the arms. A pair of elongate linkages 5244a and 5244b extend inwardly from pivots 5246a and 5246b at respective proximal ends of the arms to a pivot 5248 connecting the linkages with an elongate rod 5250. Linkages 5244a and 5244b are disposed on opposite sides of the rod, with pivot 5248 extending through the linkages and the rod and with tabs or ears 5252 extending laterally outward from the rod in opposite directions to overhang the linkages as stops preventing the linkages from spreading outwardly beyond a predetermined position. Jaws 5112 and 5114 are moved relative to one another by moving the outer tubular member and rod relative to one another. The jaws are normally biased apart, for example by a torsion spring coiled around a pivot and connected between the jaws, and are closed by moving the outer tubular member distally relative to the jaws, for example by advancing the outer tubular member distally and/or pulling the rod in the proximal direction. In a preferred embodiment, the outer tubular member is biased distally relative to the jaws so that the jaws are normally in a closed position.

From the above, it will be appreciated that the surgical instrument according to the present invention permits manipulation of anatomical tissue during endoscopic procedures without the need of having to use multiple instruments inserted through multiple puncture sites by inserting an elongate shaft carrying at least two end effector assemblies through a single puncture site. Preferably, the end effector assemblies each include a distal portion movable between an undeployed, contracted or parked position spaced laterally inward of a peripheral edge of the elongate shaft to facilitate insertion through a portal sleeve and a deployed, expanded or working position where at least part of the distal portion is spaced laterally outward of the peripheral edge of the elongate shaft to provide maximum working span. The elongate shaft is mounted by a handle with controls for moving one or both of the end effector assemblies axially and in a rotary manner. The end effector assemblies each include an end effector at a distal end. While the end effectors are described above as being forceps jaws, it will be appreciated that the end effectors can have any suitable configuration for individually or cooperatively manipulating or otherwise affecting tissue and other objects including, but not limited to, forceps, cutters, needle holders, cauteries, clip appliers, staplers, ligators and the like.

The end effector assemblies of the surgical instrument can be of the same or different design. For example, one end effector assembly can include an end effector in the form of a forceps while another end effector assembly includes an end effector in the form of a cutter. While the end effector assemblies are shown disposed within cylindrical channels formed through the elongate shaft, it will be appreciated that one or more of the end effector assemblies can be disposed within arcuate channels so that, for example, one of the end effector assemblies can be moved arcuately within the shaft about the center of curvature of the curved channel while the other end effector assembly is rotated about its longitudinal axis or vice versa. Distal portions of the end effector assemblies preferably extend laterally outward at an angle from respective longitudinal axes of the elongate shaft so that, when the end effector assemblies are rotated about their respective longitudinal axes, the end effectors at the distal ends of the assemblies are made to move arcuately along non-concentric arcuate paths which may or may not intersect dependent upon the respective lengths of the distal portions and their respective bend angles. Any type of end effector assembly can be modified for use with the surgical instrument according to the present invention by configuring a distal portion of the end effector assembly to be normally bent outwardly at an angle relative to the proximal portion, including, but not limited to, any of the end effector assemblies or drivers described in U.S. patent application Ser. No. 08/758,648, filed Nov. 27, 1996, and Ser. Nos. 08/847,182, 08/847,254, 08/847,253, 08/847,189, and 08/847,252, filed May 1, 1997, the disclosures of which are incorporated herein by reference. For example, the end effector assemblies can include a transverse connecting member extending outwardly from a proximal portion of the end effector assembly at an angle to connect with longitudinally oriented end effectors laterally offset from the proximal portion.

The end effectors can be straight, curved or angled in configuration and, when an end effector is a pair of jaws, the jaws can be provided with ribs, a diamond tread pattern or any other type of grasping surface to assure a positive grip as well as grooves, slots or holes to permit access through the jaws when the jaws are closed. The jaws can also carry cutting members, such as slots with sharp edges or protruding blades, and can have opposed arcuate or concave portions for clamping tubular objects, such as organs, without compressing the objects, as well as portions configured to take a tissue sample for biopsy.

When the end effectors are carried at the distal end of one or more elongate components, for example a rod telescopically fitted within a tube, either component can include a distal portion of predetermined shape which, in an unrestrained condition, bends laterally outward at an angle relative to the longitudinal axis of the proximal portion of the end effector component. Furthermore, components of an end effector assembly can be keyed or coupled to move together so that, for example, if one of the components is rotated the other component will be rotated as well.

The end effectors can be used alone or in combination to perform lysis of adhesion, dissection, pickup and cutting, pickup and clipping, pickup and suturing with a suture needle, unipolar and bipolar electrosurgery, and numerous other procedures. For example, the end effectors can be used in combination to perform dual electrode cauterization, to clamp tissue between adjacent end effectors, or to separate tissue by placing adjacent end effectors between tissue sections and moving the end effectors away from one another. Adjacent end effectors, acting as electrodes, can also be pressed against opposite sides of tissue to cauterize the tissue. Also, a button or switch can be provided to selectively switch the electric power between end effectors for unipolar cauterization.

Although the surgical instrument is shown and described herein as having two end effectors, it will be appreciated that the instrument can have one end effector or more than two end effectors (e.g., three or four) dependent upon the procedure to be performed and the preference of the user. Also, the end effectors can be positioned at diametrically opposed locations relative to the central longitudinal axis of the elongate shaft as shown or at any other laterally spaced positions.

Although the elongate shaft is shown as being composed of optical fibers disposed within a tubular sleeve, it will be appreciated that the elongate shaft can be formed without a separate sleeve, for example by embedding or molding the optical fibers within a medically acceptable polymer matrix or by adhesively connecting the fibers together. The elongate shaft can also be formed without optical fibers extending therethrough, in which case a light source may be inserted through one of the channels defined through the shaft or through a separate puncture to illuminate the operative site. The shaft can be rigid or flexible and can be made of any suitable medically acceptable material, such as plastic or stainless steel. The cross-sectional configuration of the outer surface of the shaft is preferably circular as shown but can be elliptical, polygonal or have any other configuration suitable for a particular purpose. The distal end or face of the shaft can be flat as shown, convex or concave; and, when flat, the distal face can be oriented at any angle relative to the longitudinal axis of the shaft. While three channels are shown in addition to the end effector channels, any number of channels can be formed through the elongate shaft, for example by thin wall, tubular sleeves extending longitudinally through the shaft or by voids or spaces defined between the optical fibers as shown. The channels can be parallel to one another or oriented at angles, can be straight or curved, and can be of constant or varying lateral dimension along their length. Furthermore, the channels can be located anywhere within the elongate shaft and can be of the same or different design dependent upon procedural use and space constraints.

The operating channels can have any configuration in transverse cross-section including, but not limited to, elliptical, polygonal and irregular or asymmetrical cross-sectional configurations. Also, all or part of the inner surface of a channel can be electrically insulated to permit passage of electrosurgical instruments therethrough. The valves and couplings shown at the proximal end of each channel are merely exemplary of the types of conventional valves and conventional couplings that can be used. Operating channels may also be defined along the length of the end effector assemblies of the instrument, if desired. It will also be appreciated that storage spaces or recesses can be defined in the elongate shaft to hold suture needles, lengths of suture material, and other devices.

While a particular handle assembly is shown and described herein for holding the instrument and controlling operation of the end effectors, it will be appreciated that other handle configurations can be used including, but not limited to, configurations wherein the handle includes pivoted legs with finger loops, one fixed and one pivoted leg with finger loops, a pistol grip with one or more movable triggers, and/or resilient U-shaped handle members. It is also possible to mount handle members on both sides of the handle housing so that operation of the end effector assemblies is controlled by separate pairs of handle members as described, for example, in application Ser. No. 08/847,254, the disclosure of which is incorporated herein by reference. Moreover, the handle can have adjustable handle members of variable orientation as shown or handle members which are fixed in a specific orientation relative to the housing. If desired, the housing and at least a portion of the handle can be formed as an integral one-piece unit.

While the end effector assemblies have been described above as being independently controlled by operating mechanisms such as push buttons and collars which, for the most part, must be operated with both hands, it will be appreciated that a single operating mechanism can be used to synchronize movement of the end effector assemblies relative to one another as well as operation of their respective end effectors when appropriate to further simplify the surgical process by allowing one-hand operation of the instrument.

Moving the end effectors of the present invention relative to one another can be accomplished in any suitable manner, for example by connecting a knob at the proximal end of each end effector assembly and sliding the knobs along slots formed in the handle housing or by mounting the end effector assemblies on geared components and moving the gears with a trigger or some other handle member or device.

While the end effector assemblies have been described herein as having a normally bent configuration which can be straightened by retracting the end effector assemblies in a proximal direction relative to a tubular member so as to elastically deform the end effector assemblies, it will be appreciated that the end effector assemblies of the present invention can be moved between contracted and expanded positions using any suitable method including, but not limited to, methods utilizing linkages, gears, cables, movable stiffeners or inserts, shape memory materials, actuators or motors. Dependent upon the angular deflection and length of the bent or angled distal portions of the end effector assemblies, the distal portions may be movable between deployed and parked positions merely by rotation about their respective axes. Also, distal portions of the end effector assemblies need not be straight as shown but can be curved or multiply angled, if desired.

The components of the surgical instrument of the present invention can be made of any suitable, medical grade materials to permit sterilization for reuse or disposal for single patient use. The components can be made of multiple parts of various configurations and materials to reduce cost. The housing and/or handle can have various valves, stop cocks and seals therein to control the flow of fluid and medical devices through the surgical instrument.

The features of the various embodiments described above can be combined in any manner desired dependent upon the operational requirements of the procedure to be performed and the complexity of the surgical instrument.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A surgical instrument for use in open and endoscopic surgery comprising
   a housing;
   an elongate shaft having a proximal end mounted by said housing and a distal end with a peripheral edge;
   a first end effector assembly protruding from said distal end of said elongate shaft and having an end effector at a distal end; and
   a second end effector assembly protruding from said distal end of said elongate shaft and having an end effector at a distal end;
   wherein a distal portion of said first end effector assembly extends laterally outward at an angle from a first longitudinal axis of said elongate shaft to a position where at least a portion of said corresponding end effector is spaced laterally outward of said peripheral edge of said elongate shaft; and
   wherein said first end effector assembly is rotatable about said first longitudinal axis of said elongate shaft to cause said corresponding end effector to move along a first arcuate path having a center of curvature coaxial with said first longitudinal axis.

2. A surgical instrument as recited in claim 1 wherein said end effector of said first end effector assembly is movable between an undeployed position where said end effector is spaced laterally inward of said peripheral edge of said elongate shaft and a deployed position where at least a portion of said end effector is disposed laterally outward of said peripheral edge.

3. A surgical instrument as recited in claim 2 wherein said first end effector assembly includes an elongate proximal portion extending at least partly through said shaft in coaxial alignment with said first longitudinal axis.

4. A surgical instrument as recited in claim 3 wherein said first end effector assembly is longitudinally movable relative to said elongate shaft between an axially extended position where said distal portion of said first end effector assembly bends outwardly in a lateral direction relative to said first longitudinal axis and an axially retracted position where said distal portion of said first end effector assembly is drawn laterally inward toward said first longitudinal axis.

5. A surgical instrument as recited in claim 4 wherein said end effector of said first end effector assembly is proximally spaced from said distal end of said shaft in said retracted position.

6. A surgical instrument as recited in claim 1 wherein said second end effector assembly extends laterally outward at an angle from a second longitudinal axis of said elongate shaft to a position where at least a portion of said corresponding end effector is spaced laterally outward of said peripheral edge of said elongate shaft.

7. A surgical instrument as recited in claim 6 wherein said second end effector assembly is rotatable about said second longitudinal axis of said elongate shaft to cause said corresponding end effector to move along a second arcuate path having a center of curvature coaxial with said second longitudinal axis.

8. A surgical instrument as recited in claim 6 wherein said end effector of said second end effector assembly is movable between an undeployed position where said end effector is spaced laterally inward of said peripheral edge of said elongate shaft and a deployed position where at least a portion of said end effector is disposed laterally outward of said peripheral edge.

9. A surgical instrument as recited in claim 8 wherein said second end effector assembly includes an elongate proximal portion extending at least partly through said shaft in coaxial alignment with said second longitudinal axis.

10. A surgical instrument as recited in claim 9 wherein said second end effector assembly is longitudinally movable relative to said elongate shaft between an axially extended position where said distal portion of said second end effector assembly bends outwardly in a lateral direction relative to said second axis of rotation and an axially retracted position where said distal portion of said second end effector assembly is drawn inwardly toward said second axis of rotation.

11. A surgical instrument as recited in claim 10 wherein said end effector of said second end effector assembly is proximally spaced from said distal end of said shaft in said retracted position.

12. A surgical instrument as recited in claim 1 and further comprising an operating channel defined through said elongate shaft to provide access to the operative site from outside the body.

13. A surgical instrument as recited in claim 1 and further comprising a plurality of operating channels defined through said elongate shaft in laterally spaced relation to provide access to the operative site from outside the body.

14. A surgical instrument as recited in claim 12 wherein said operating channel extends through said housing to define a longitudinal channel along the length of said instrument, and further comprising a coupling at a proximal end of said channel.

15. A surgical instrument as recited in claim 12 wherein said operating channel extends through said housing to define a longitudinal channel along the length of said instrument, and further comprising a valve disposed along said longitudinal channel to control passage of fluids and instruments therethrough.

16. A surgical instrument as recited in claim 1 wherein an operating channel is defined through one of said end effector assemblies to provide access to the operative site from outside the body.

17. A surgical instrument as recited in claim 16 wherein said end effector assembly having an operating channel defined therethrough includes an elongate proximal portion extending through said elongate shaft and wherein said operating channel terminates distally at an opening adjacent the junction between said proximal and distal portions of said end effector assembly.

18. A surgical instrument for use in open and endoscopic procedures comprising a housing;

an elongate shaft having a proximal end mounted by said housing and a distal end with a peripheral edge;

a first end effector assembly having a proximal portion extending at least part way through said elongate shaft along a first longitudinal axis, a distal portion extending laterally outward from said proximal portion at an angle, and a end effector mounted on said distal portion, said proximal portion of said first end effector assembly being rotatably mounted within said elongate shaft to move said end effector of said first end effector assembly along a first arcuate path having a center of curvature coaxial with said first longitudinal axis; and a second end effector assembly having a proximal portion extending at least part way through said elongate shaft along a second longitudinal axis laterally spaced from said first longitudinal axis, a distal portion extending laterally outward from said proximal portion at an angle, and a end effector mounted on said distal portion, said proximal portion of said second end effector assembly being rotatably mounted within said elongate shaft to move said end effector of said second end effector assembly along a second arcuate path having a center of curvature coaxial with said second longitudinal axis;

wherein said first arcuate path has a radius of curvature causing at least a portion of said end effector of said first end effector assembly to extend outwardly of said peripheral edge of said elongate shaft.

19. A surgical instrument as recited in claim 18 wherein said second arcuate path has a radius of curvature causing at least a portion of said end effector of said second end effector assembly to extend outwardly of said peripheral edge of said elongate shaft.

20. A surgical instrument as recited in claim 18 wherein said respective end effectors of said first and second end effector assemblies are movable between undeployed positions where said end effectors are spaced laterally inward of said peripheral edge of said elongate shaft and deployed positions where at least a portion of each of said end effectors is disposed laterally outward of said peripheral edge.

21. A surgical instrument as recited in claim 18 wherein said first and second end effector assemblies are longitudinally movable relative to said elongate shaft between respective axially extended positions where respective distal portions of said first and second end effector assemblies bend outwardly in a lateral direction relative to said first and second longitudinal axes, respectively, and respective axially retracted positions where said distal portions are drawn inwardly toward said first and second longitudinal axes, respectively.

22. A surgical instrument as recited in claim 21 wherein said end effectors of said first and second end effector assemblies are proximally spaced from said distal end of said elongate shaft in said respective retracted positions.

23. A method of performing a surgical procedure in an anatomical cavity comprising the steps of introducing a surgical instrument having an elongate shaft into the anatomical cavity, the surgical instrument including first and second end effector assemblies protruding distally from the distal end of the elongate shaft, the first end effector assembly including a distal portion extending laterally outward at an angle from a first longitudinal axis of the elongate shaft to an end effector disposed at least partly outside a peripheral edge of the elongate shaft; and operating on tissue within the anatomical cavity by rotating the first end effector assembly about the first longitudinal axis.

24. A method of performing a surgical procedure as recited in claim 23 and further comprising, prior to said operating step, the step of moving the first end effector assembly laterally outward from an undeployed position spaced laterally inward of the peripheral edge of the elongate shaft to a deployed position spaced laterally outward of the peripheral edge of the elongate shaft.

25. A method of performing a surgical procedure as recited in claim 23 and further comprising, prior to said operating step, the step of moving the first end effector assembly distally relative to the elongate shaft from an axially retracted position within the elongate shaft to an axially extended position protruding from the distal end of the elongate shaft.

26. A method of performing a surgical procedure as recited in claim 23 wherein the second end effector assembly includes a distal portion extending laterally outward at an angle from a second longitudinal axis of the elongate shaft to an end effector disposed at least partly outside a peripheral edge of the elongate shaft and further comprising the step of operating on the tissue by rotating the second end effector assembly about the second longitudinal axis of the elongate shaft.

27. A method of performing a surgical procedure as recited in claim 23 and further comprising the step of operating on the tissue by moving the second end effector assembly axially relative to the first end effector assembly.

28. A method of performing a surgical procedure as recited in claim 23 and further comprising the step of operating on the tissue by moving the first end effector assembly axially relative to the second end effector assembly.

29. A method of performing a surgical procedure as recited in claim 23 and further comprising the step of operating on the tissue by rotating the shaft.

30. A method of performing a surgical procedure as recited in claim 26 wherein said steps of operating on the tissue are conducted simultaneously.

31. A surgical instrument as recited in claim 1, further comprising an operating mechanism coupled to said first arm and said second arm for creating synchronized movement of said end effectors and a push button for actuating said ope rating mechanism.

32. A surgical instrument for use in open and endoscopic procedures, comprising:

an elongate shaft having a proximal end and a distal end with a peripheral edge;

a handle coupled to said proximal end of said shaft;

a first arm protruding from said distal end of said elongate shaft and having an end effector at a distal end; and a second arm protruding from said distal end of said elongate shaft and having an end effector at a distal end;

wherein said first arm extends laterally outward at an angle from a first longitudinal axis within said elongate shaft to a position where at least a portion of said end effector of said first arm is spaced laterally outward of said peripheral edge of said elongate shaft; and wherein said first arm is rotatable about said first longitudinal axis to cause said end effector of said first arm to move along a first arcuate path having a center of curvature coaxial with said first longitudinal axis.

33. A surgical instrument as recited in claim 1, wherein said end effector of said first arm is movable between an undeployed position where said end effector is spaced laterally inward of said peripheral edge of said elongate shaft and a deployed position where at least a portion of said end effector of said first arm is disposed laterally outward of said peripheral edge.

34. A surgical instrument as recited in claim 2, wherein said first arm is coupled to an elongate proximal member extending at least partly through said shaft in coaxial alignment with said first longitudinal axis.

35. A surgical instrument as recited in claim 3, wherein said first arm is longitudinally movable relative to said elongate shaft between an axially extended position where said first arm extends outwardly in a lateral direction relative to said first longitudinal axis and an axially retracted position where said first arm is moved laterally inward toward said first longitudinal axis.

36. A surgical instrument as recited in claim 4, wherein said end effector of said first arm is proximally spaced from said distal end of said shaft in said retracted position.

37. A surgical instrument as recited in claim 1, wherein said second arm extends laterally outward at an angle from a second longitudinal axis within said elongate shaft to a position where at least a portion of said end effector of said second arm is spaced laterally outward of said peripheral edge of said elongate shaft.

38. A surgical instrument as recited in claim 6, wherein said second arm is rotatable about said second longitudinal axis to cause said end effector of said second arm to move along a second arcuate path having a center of curvature coaxial with said second longitudinal axis.

39. A surgical instrument as recited in claim 6, wherein said end effector of said second arm is movable between an undeployed position where said end effector is spaced laterally inward of said peripheral edge of said elongate shaft and a deployed position where at least a portion of said end effector is disposed laterally outward of said peripheral edge.

40. A surgical instrument as recited in claim 8, wherein said second arm is coupled to an elongate proximal member extending at least partly through said shaft in coaxial alignment with said second longitudinal axis.

41. A surgical instrument as recited in claim 9, wherein said second arm is longitudinally movable relative to said elongate shaft between an axially extended position where said distal portion of said second arm extends outwardly in a lateral direction relative to said second longitudinal axis and an axially retracted position where said distal portion of said second end effector assembly is moved inwardly toward said second longitudinal axis.

42. A surgical instrument as recited in claim 10, wherein said end effector of said second arm is proximally spaced from said distal end of said shaft in said retracted position.

43. A surgical instrument as recited in claim 1 and further comprising an operating channel defined through said elongate shaft to provide access to an operative site in a patients' body into which the distal end of the elongate shaft is inserted.

44. A surgical instrument as recited in claim 1 and further comprising a plurality of operating channels defined through said elongate shaft in laterally spaced relation to provide access to an operative site in a patients' body into which the distal end of the elongate shaft is inserted.

45. A surgical instrument as recited in claim 12 further comprising a coupling at a proximal end of said operating channel.

46. A surgical instrument as recited in claim 12 and further comprising a valve disposed along said operating channel to control passage of fluids and instruments therethrough.

47. A surgical instrument as recited in claim 1, wherein an operating channel is defined through one of said arms to provide access to an operative in a patients' body into which the distal end of the elongate shaft is inserted.

48. A surgical instrument as recited in claim 16, wherein said arm having an operating channel defined therethrough is coupled to an elongate proximal member extending through said elongate shaft and wherein said operating channel terminates distally at an opening adjacent the junction between said arm and said proximal member.

49. A surgical instrument for use in open and endoscopic procedures, comprising:

an elongate shaft having a proximal end and a distal end with a peripheral edge;

a handle coupled to said proximal end of said shaft;

a first end effector assembly having a proximal portion extending at least part way through said elongate shaft along a first longitudinal axis, a distal arm portion extending laterally outward from said proximal portion at an angle, and a end effector mounted on said distal arm portion, said proximal portion of said first end effector assembly being rotatably mounted within said elongate shaft to move said end effector of said first end effector assembly along a first arcuate path having a center of curvature coaxial with said first longitudinal axis;

a second end effector assembly having a proximal portion extending at least part way through said elongate shaft along a second longitudinal axis laterally spaced from said first longitudinal axis, a distal arm portion extending laterally outward from said proximal portion at an angle, and an end effector mounted on said distal arm portion, said proximal portion of said second end effector assembly being rotatably mounted within said elongate shaft to move said end effector of said second end effector assembly along a second arcuate path having a center of curvature coaxial with said second longitudinal axis; and wherein said first arcuate path has a radius of curvature causing at least a portion of said end effector of said first end effector assembly to extend outwardly of said peripheral edge of said elongate shaft.

50. A surgical instrument as recited in claim 18, wherein said first and second end effector assemblies are longitudinally movable relative to said elongate shaft between respective axially extended positions where respective distal arm portions of said first and second end effector assemblies bend outwardly in a lateral direction relative to said first and second longitudinal axes, respectively, and respective axially retracted positions where said distal arm portions are drawn inwardly toward said first and second longitudinal axes, respectively.

51. A method of performing a surgical procedure in an anatomical cavity, comprising the steps of:

introducing a surgical instrument having an elongate shaft into the anatomical cavity, the surgical instrument including first and second arms protruding distally from the distal end of the elongate shaft, the first arm extending laterally outward at an angle from a first longitudinal axis within the elongate shaft and having an end effector thereon disposed at least partly outside a peripheral edge of the elongate shaft; and operating on tissue within the anatomical cavity by rotating the first arm about the first longitudinal axis.

52. A method of performing a surgical procedure as recited in claim 23 and further comprising, prior to said operating step, the step of:

moving the first arm laterally outward from an undeployed position spaced laterally inward of the peripheral edge of the elongate shaft to a deployed position spaced laterally outward of the peripheral edge of the elongate shaft.

53. A method of performing a surgical procedure as recited in claim 23 and further comprising, prior to said operating step, the step of:

moving the first arm distally relative to the elongate shaft from an axially retracted position within the elongate shaft to an axially extended position protruding from the distal end of the elongate shaft.

54. A method of performing a surgical procedure as recited in claim 23, wherein the second arm extends laterally outward at an angle from a second longitudinal axis within the elongate shaft and has an end effector disposed thereon at least partly outside a peripheral edge of the elongate shaft and further comprising the step of operating on the tissue by rotating the second arm about the second longitudinal axis of the elongate shaft.

55. A method of performing a surgical procedure as recited in claim 23 and further comprising the step of operating on the tissue by moving the second arm axially relative to the elongate shaft.

56. A method of performing a surgical procedure as recited in claim 23 and further comprising the step of operating on the tissue by moving the first arm axially relative to the elongate shaft.

\* \* \* \* \*